US012702349B2

(12) United States Patent
Belding et al.

(10) Patent No.: US 12,702,349 B2
(45) Date of Patent: Aug. 11, 2026

(54) SYSTEMS AND METHODS FOR MONITORING AND TREATING DIABETIC FOOT ULCERS

(71) Applicant: T.J.Smith and Nephew,Limited, Hull (GB)

(72) Inventors: Jonathan Edward Mika Belding, Dorchester (GB); Johannes Dagevos van Rij, Skidby (GB); Allan Kenneth Frazer Grugeon Hunt, Beverley (GB); Jonathon Simon Lay, Beckenham (GB); Brian William Quist, Andover, MA (US); Damian Lawson Smith, Swanland (GB)

(73) Assignee: T.J.Smith and Nephew, Limited, Hull (GB)

( * ) Notice: Subject to any disclaimer, the term of this patent is extended or adjusted under 35 U.S.C. 154(b) by 1171 days.

(21) Appl. No.: 17/613,446

(22) PCT Filed: May 21, 2020

(86) PCT No.: PCT/EP2020/064228
§ 371 (c)(1),
(2) Date: Nov. 22, 2021

(87) PCT Pub. No.: WO2020/234429
PCT Pub. Date: Nov. 26, 2020

(65) Prior Publication Data

US 2022/0304621 A1 Sep. 29, 2022

Related U.S. Application Data

(60) Provisional application No. 62/889,955, filed on Aug. 21, 2019.

(30) Foreign Application Priority Data

May 23, 2019 (GB) ..................................... 1907254
May 23, 2019 (GB) ..................................... 1907260

(51) Int. Cl.
*A61B 5/00* (2006.01)
*A61B 5/103* (2006.01)
*A61B 5/11* (2006.01)

(52) U.S. Cl.
CPC ............ *A61B 5/445* (2013.01); *A61B 5/1036* (2013.01); *A61B 5/1114* (2013.01);
(Continued)

(58) Field of Classification Search
CPC ..... A61B 5/445; A61B 5/1036; A61B 5/1114; A61B 5/1118; A61B 5/447; A61B 5/4561;
(Continued)

(56) References Cited

U.S. PATENT DOCUMENTS 3,974,491 A 8/1976 Sipe
4,610,253 A 9/1986 Rosenberg
(Continued)

FOREIGN PATENT DOCUMENTS

CN 105631195 B 12/2017
CN 105997094 B 3/2019
(Continued)

OTHER PUBLICATIONS

International Preliminary Report on Patentability for Application No. PCT/EP2020/064228, mailed on Dec. 2, 2021, 14 pages.
(Continued)

*Primary Examiner* — Abid A Mustansir
(74) *Attorney, Agent, or Firm* — Knobbe, Martens, Olson & Bear, LLP

(57) ABSTRACT

In some aspects, a computer-implemented method is disclosed for gathering and processing sensor data to identify a risk of impacting or causing a skin injury. The computer-implemented method can include: receiving, via a computer network, sensor feature data representing output of a user sensor configured to be worn on a limb of a user; generating
(Continued)

activity classification model output data using the sensor feature data and an activity classification model, the activity classification model output data representing likelihoods that the sensor feature data corresponds to each of a plurality of different activity classifications; determining an activity classification from the activity classification model output data; and transmitting, via the computer network, display data representing the activity classification to a computing device configured to present the display data.

21 Claims, 6 Drawing Sheets

(52) U.S. Cl.
CPC ............ *A61B 5/1118* (2013.01); *A61B 5/447* (2013.01); *A61B 5/4561* (2013.01); *A61B 5/6812* (2013.01); *A61B 5/7264* (2013.01); *A61B 5/7275* (2013.01); *A61B 5/742* (2013.01); *A61B 2562/0219* (2013.01)

(58) Field of Classification Search
CPC ... A61B 5/6812; A61B 5/7264; A61B 5/7275; A61B 5/742; A61B 2562/0219; A61B 5/684; A61B 2503/22; A61B 5/1123; A61B 5/6828; A61B 5/6829; A61B 5/1115; A61B 5/6802; A61B 5/7235; A61B 5/7267
See application file for complete search history.

(56) References Cited

U.S. PATENT DOCUMENTS

| | | | | |
|---|---|---|---|---|
| 5,107,854 | A | 4/1992 | Knotts et al. | |
| 5,253,654 | A | 10/1993 | Thomas et al. | |
| 5,642,096 | A | 6/1997 | Leyerer et al. | |
| 5,875,571 | A | 3/1999 | Huang | |
| 5,879,292 | A | 3/1999 | Sternberg et al. | |
| 6,031,463 | A | 2/2000 | Bechmann | |
| 6,282,448 | B1 | 8/2001 | Katz et al. | |
| 6,287,253 | B1 | 9/2001 | Ortega et al. | |
| 6,571,193 | B1 | 5/2003 | Unuma et al. | |
| 6,602,191 | B2 | 8/2003 | Quy | |
| 7,616,110 | B2 | 11/2009 | Crump et al. | |
| 7,998,092 | B2 | 8/2011 | Avni et al. | |
| 8,111,165 | B2 | 2/2012 | Ortega et al. | |
| 8,280,682 | B2 | 10/2012 | Vock et al. | |
| 8,388,553 | B2 | 3/2013 | James et al. | |
| 8,753,275 | B2 | 6/2014 | Najafi et al. | |
| 8,925,392 | B2 | 1/2015 | Esposito et al. | |
| 9,220,455 | B2 | 12/2015 | Sarrafzadeh et al. | |
| 9,338,819 | B2 | 5/2016 | Meng et al. | |
| 9,427,179 | B2 | 8/2016 | Mestrovic et al. | |
| 9,439,599 | B2 | 9/2016 | Thompson et al. | |
| 9,629,585 | B2 | 4/2017 | Das et al. | |
| 9,861,550 | B2 | 1/2018 | Ribble et al. | |
| 9,907,103 | B2 | 2/2018 | Chen et al. | |
| 10,019,555 | B2 | 7/2018 | Manice et al. | |
| 10,085,675 | B2 | 10/2018 | Nagasaki et al. | |
| 10,166,164 | B2 | 1/2019 | Johnson et al. | |
| 10,274,305 | B2 | 4/2019 | Huang et al. | |
| 10,335,636 | B2 | 7/2019 | Holma et al. | |
| 12,114,995 | B2 | 10/2024 | Walgreen et al. | |
| 2003/0088294 | A1 | 5/2003 | Gesotti | |
| 2005/0099294 | A1 | 5/2005 | Bogner et al. | |
| 2005/0165284 | A1 | 7/2005 | Gefen | |
| 2006/0052678 | A1 | 3/2006 | Drinan et al. | |
| 2007/0173903 | A1 | 7/2007 | Goren et al. | |
| 2008/0216593 | A1 | 9/2008 | Jacobsen et al. | |
| 2008/0287832 | A1 | 11/2008 | Collins et al. | |
| 2009/0069727 | A1 | 3/2009 | Neustaedter et al. | |
| 2009/0070939 | A1 | 3/2009 | Hann | |
| 2009/0209830 | A1 | 8/2009 | Nagle et al. | |
| 2009/0234249 | A1 | 9/2009 | Randolph | |
| 2009/0234262 | A1 | 9/2009 | Reid, Jr. et al. | |
| 2009/0292194 | A1 | 11/2009 | Libbus et al. | |
| 2009/0326339 | A1 | 12/2009 | Horvitz | |
| 2010/0056873 | A1 | 3/2010 | Allen et al. | |
| 2010/0099956 | A1 | 4/2010 | Cole et al. | |
| 2010/0162832 | A1 | 7/2010 | Brauers | |
| 2010/0198022 | A1 | 8/2010 | Vuillerme et al. | |
| 2010/0225476 | A1 | 9/2010 | Klose | |
| 2010/0298742 | A1 | 11/2010 | Perlman et al. | |
| 2010/0305480 | A1 | 12/2010 | Fu et al. | |
| 2010/0324455 | A1 | 12/2010 | Rangel et al. | |
| 2011/0054359 | A1 | 3/2011 | Sazonov et al. | |
| 2011/0130697 | A1 | 6/2011 | Nagle et al. | |
| 2011/0214501 | A1 | 9/2011 | Ross et al. | |
| 2011/0263950 | A1 | 10/2011 | Larson et al. | |
| 2012/0010535 | A1 | 1/2012 | Kubiak et al. | |
| 2012/0109013 | A1 | 5/2012 | Everett et al. | |
| 2012/0185267 | A1 | 7/2012 | Kamen et al. | |
| 2012/0203491 | A1 | 8/2012 | Sun et al. | |
| 2012/0238914 | A1 | 9/2012 | Goldfield et al. | |
| 2012/0259651 | A1 | 10/2012 | Mallon et al. | |
| 2013/0023720 | A1 | 1/2013 | Solomon et al. | |
| 2013/0167848 | A1 | 7/2013 | Frassica et al. | |
| 2013/0213145 | A1 | 8/2013 | Owings et al. | |
| 2013/0282324 | A1 | 10/2013 | Carter et al. | |
| 2013/0317753 | A1 | 11/2013 | Kamen et al. | |
| 2014/0089673 | A1 | 3/2014 | Luna | |
| 2014/0107932 | A1 | 4/2014 | Luna | |
| 2014/0135657 | A1 | 5/2014 | Wu et al. | |
| 2014/0188499 | A1 | 7/2014 | Bell et al. | |
| 2014/0200486 | A1 | 7/2014 | Bechtel et al. | |
| 2014/0203797 | A1 | 7/2014 | Stivoric et al. | |
| 2014/0221787 | A1 | 8/2014 | Teller et al. | |
| 2014/0235166 | A1 | 8/2014 | Molettiere et al. | |
| 2014/0303460 | A1 | 10/2014 | Corley et al. | |
| 2014/0350435 | A1 | 11/2014 | Lam | |
| 2014/0372147 | A1 | 12/2014 | White | |
| 2014/0378786 | A1 | 12/2014 | Hong et al. | |
| 2015/0094545 | A1 | 4/2015 | Russell et al. | |
| 2015/0125839 | A1 | 5/2015 | Tillges et al. | |
| 2015/0182843 | A1 | 7/2015 | Esposito et al. | |
| 2016/0092651 | A1 | 3/2016 | Austin et al. | |
| 2016/0120433 | A1 | 5/2016 | Hughes et al. | |
| 2016/0135731 | A1 | 5/2016 | Drennan | |
| 2016/0213924 | A1 | 7/2016 | Coleman et al. | |
| 2016/0228050 | A1 | 8/2016 | Sugla et al. | |
| 2016/0256080 | A1 | 9/2016 | Shen et al. | |
| 2016/0275776 | A1 | 9/2016 | Shen et al. | |
| 2016/0296144 | A1 | 10/2016 | Gaddam et al. | |
| 2016/0317083 | A1 | 11/2016 | DeLuke et al. | |
| 2016/0317084 | A1 | 11/2016 | DeLuke et al. | |
| 2016/0331322 | A1 | 11/2016 | Son et al. | |
| 2016/0338621 | A1* | 11/2016 | Kanchan | A61B 5/11 |
| 2016/0367192 | A1 | 12/2016 | Iyengar et al. | |
| 2017/0011210 | A1 | 1/2017 | Cheong et al. | |
| 2017/0027498 | A1 | 2/2017 | Larson et al. | |
| 2017/0027529 | A1 | 2/2017 | Frieder et al. | |
| 2017/0046503 | A1 | 2/2017 | Cho et al. | |
| 2017/0055851 | A1 | 3/2017 | Al-Ali | |
| 2017/0056724 | A1 | 3/2017 | Baker | |
| 2017/0160400 | A1* | 6/2017 | Larbi | A61F 5/0111 |
| 2017/0225033 | A1 | 8/2017 | Czaja | |
| 2017/0231015 | A1 | 8/2017 | Jang et al. | |
| 2017/0281073 | A1 | 10/2017 | Drennan et al. | |
| 2017/0347899 | A1 | 12/2017 | Bhushan et al. | |
| 2017/0367644 | A1 | 12/2017 | Sharman et al. | |
| 2018/0000407 | A1 | 1/2018 | Johnson et al. | |
| 2018/0020931 | A1 | 1/2018 | Shusterman | |
| 2018/0025146 | A1 | 1/2018 | Vasyltsov et al. | |
| 2018/0074547 | A1 | 3/2018 | Smadi et al. | |
| 2018/0125423 | A1 | 5/2018 | Chang et al. | |
| 2018/0132287 | A1 | 5/2018 | Cheng et al. | |
| 2018/0185558 | A1 | 7/2018 | Weston | |
| 2018/0271409 | A1 | 9/2018 | Gong et al. | |
| 2018/0360157 | A1 | 12/2018 | Jeong et al. | |
| 2019/0082771 | A1 | 3/2019 | Shin et al. | |

(56) References Cited

U.S. PATENT DOCUMENTS

| | | | |
|---|---|---|---|
| 2021/0100496 | A1 | 4/2021 | Hartwell et al. |
| 2023/0157897 | A1 | 5/2023 | Engel et al. |

FOREIGN PATENT DOCUMENTS

| | | | |
|---|---|---|---|
| CN | 110025316 | A | 7/2019 |
| DE | 19612334 | A1 | 1/1997 |
| DE | 102013013013 | A1 | 2/2015 |
| DE | 102014222955 | A1 | 5/2016 |
| EP | 2675315 | B1 | 5/2020 |
| EP | 3972483 | A2 | 3/2022 |
| GB | 2439750 | A | 1/2008 |
| JP | 2005245709 | A | 9/2005 |
| JP | 2009125506 | A | 6/2009 |
| JP | 2014046151 | A | 3/2014 |
| WO | WO-2005121729 | A1 | 12/2005 |
| WO | WO-2013064852 | A1 | 5/2013 |
| WO | WO-2013123263 | A1 | 8/2013 |
| WO | WO-2014178755 | A1 | 11/2014 |
| WO | WO-2016018448 | A1 | 2/2016 |
| WO | WO-2016087381 | A1 | 6/2016 |
| WO | WO-2016154230 | A1 | 9/2016 |
| WO | WO-2016180073 | A1 | 11/2016 |
| WO | WO-2016186904 | A1 | 11/2016 |
| WO | WO-2017048979 | A1 | 3/2017 |
| WO | WO-2017161037 | A1 | 9/2017 |
| WO | WO-2017205728 | A1 | 11/2017 |
| WO | WO-2017214188 | A1 | 12/2017 |
| WO | WO-2018033794 | A1 | 2/2018 |
| WO | WO-2018096390 | A1 | 5/2018 |
| WO | WO-2018144946 | A1 | 8/2018 |
| WO | WO-2018162736 | A1 | 9/2018 |
| WO | WO-2019042790 | A1 | 3/2019 |
| WO | WO-2019096828 | A1 | 5/2019 |
| WO | WO-2019162272 | A1 | 8/2019 |
| WO | WO-2019234011 | A1 | 12/2019 |
| WO | WO-2019238927 | A1 | 12/2019 |
| WO | WO-2019243171 | A1 | 12/2019 |
| WO | WO-2020159677 | A1 | 8/2020 |
| WO | WO-2020221595 | A1 | 11/2020 |

OTHER PUBLICATIONS

Abbott Diabetes Care Ltd., "FreeStyle Libre Flash Glucose Monitoring System—User's Manual," Mar. 2014, 124 pages.

Amjadi M., et al., "Ultra-Stretchable and Skin-Mountable Strain Sensors Using Carbon Nanotubes-Ecoflex Nanocomposites," Nanotechnology, Institute of Physics Publishing, vol. 26, No. 37, Aug. 25, 2015, 11 pages.

Centauri Medical, Inc., "DynaSense—Instructions for Use," Document No. 1312AJ (User Manual), Jul. 2013, 54 pages.

Crews R., et al., "A Method for Assessing Off-loading Compliance," Journal of the American Podiatric Medical Association, vol. 99 (2), Mar./Apr. 2009, 6 pages.

Crews R., et al., "Role and Determinants of Adherence to Off-loading in Diabetic Foot Ulcer Healing: A Prospective Investigation," Diabetes Care, vol. 39, Aug. 2016, pp. 1371-1377 (7 pages).

Fitbit, "Introducing Fitbit Coach," YouTube, retrieved from https://www.youtube.com/watch?v=QDYxWeQMrAw, Oct. 24, 2017, 1 page.

Hanft J., et al., "A Guide to Preventative Offloading of Diabetic Foot Ulcers," Podiatry Today, Nov. 2011, retrieved from www.podiatrytoday.com/guide-preventative-offloading-diabetic-foot-ulcers, 8 pages.

International Search Report and Written Opinion for Application No. PCT/EP2020/064228, mailed on Dec. 21, 2020, 23 pages.

Kosecki D., "9 Things You Need to Know About Your New Fitbit Coach Subscription," Fitbit, Dec. 22, 2017, retrieved from https://blog.fitbit.com/new-fitbit-coach/, 12 pages.

Muscillo R., et al., "An Adaptive Kalman-Based Bayes Estimation Technique to Classify Locomotor Activities in Young and Elderly Adults Through Accelerometers," Medical Engineering & Physics, Butterworth-Heinemann, GB, vol. 32, No. 8, Oct. 1, 2010 (Oct. 1, 2010), pp. 849-859, XP027267622, ISSN:1350-4533 [retrieved on Jun. 23, 2010] the whole document.

Nakamoto., H., et al., "Stretchable Strain Sensor with Anisotropy and Application for Joint Angle Measurement," IEEE Sensors Journal, vol. 16, No. 10, May 2016, pp. 3572-3579.

Raviglione A., et al., "Real-Time Smart Textile-Based System to Monitor Pressure Offloading of Diabetic Foot Ulcers," Journal of Diabetes Science and Technology, vol. 11, Sep. 2017, 5 pages.

Smith and Nephew Medical Ltd., "Sandy 2012980—Healthcare Professional User Manual," Jul. 2018, retrieved from https://apps.fcc.gov/oetcf/eas/reports/ViewExhibitReport.cfm?mode=Exhibits&calledFromFrame=N&application_id=f%2FbhDROytnS96PwjOmDTNA%3D%3D&fcc_id=2AEAJ-2012980, retrieved on Aug. 22, 2018, 8 pages.

Tairych A., et al., "Distributed Sensing: Multiple Capacitive Stretch Sensors on a Single Channel," Proceedings of SPIE, vol. 10163, Apr. 17, 2017, pp. 1016306-1-1016306-10.

Votzke C., et al., "Highly-Stretchable Biomechanical Strain Sensor Using Printed Liquid Metal Paste," IEEE Biomedical Circuits and Systems Conference (BIOCAS), Oct. 17, 2018, XP033483141, 4 pages.

Bancroft J.B., et al., "Activity and Environment Classification Using Foot Mounted Navigation Sensors," Indoor Positioning and Indoor Navigation (IPIN), 2012 International Conference On, IEEE, Nov. 13 -15, 2012, 10 Pages, XP032313208, DOI: 10.1109/IPIN.2012.6418902 ISBN: 978-1-4673-1955-3.

* cited by examiner

EVENT RECORDATION PROCESS

ROM(S)
630

INPUT/OUTPUT
DEVICE(S)
620

CPU(S)
610

NETWORK
CONNECTION(S)
640

NETWORK INTERFACE(S)
642

MEDIA DRIVE(S)
680

DISPLAY(S)
650

DATABASE(S)
690

690A-N

MEMORY SPACE(S)
660

OPERATING SYSTEM(S)
662

APPLICATION(S)
664

DATA
668

COMPUTER(S)
670

SYSTEMS AND METHODS FOR MONITORING AND TREATING DIABETIC FOOT ULCERS

CROSS-REFERENCE TO RELATED APPLICATIONS

This application is a U.S. national stage application of International Patent Application No. PCT/EP2020/064228, filed May 21, 2020, which claims priority to U.K. Provisional Application Nos. 1907260.2 and 1907254.5 filed on May 23, 2019, and U.S. Provisional Application No. 62/889,955 filed on Aug. 21, 2019; the disclosures of which are hereby incorporated by reference in their entirety.

TECHNICAL FIELD

Embodiments of the present disclosure relate to apparatuses, systems, and methods for managing wounds with user activity monitoring devices.

BACKGROUND

Pressure ulcers, which may also be known as pressure sores, bedsores, or decubitus ulcers, are injuries to skin and underlying tissue resulting from prolonged pressure on the skin, soft tissue, muscle, or bone above capillary filling pressure (approximately 32 mmHg).

One type of pressure ulcer that develops on a foot is known as a diabetic foot ulcer (DFU), which tends to occur with a higher frequency and intensity in the diabetic population. Management and treatment of diabetic foot ulcers requires offloading the diabetic foot ulcers by using cushioned footwear, such as a support boot, cast, shoe, or the like. While offloading can be effective, it has been found that non-compliance with or non-use of the offloading devices can play a large role in the delayed healing of the diabetic foot ulcers.

Prior art approaches and systems provide little or no information regarding an individual's lifestyle and compliance with the offloading devices. Gaining insight into the individual's lifestyle can be important for the prevention and healing of pressure ulcers. However, because of these limitations, the prevention and healing of pressure ulcers using prior art approaches and systems may be delayed or, worse yet, worsened leading to prolonged discomfort, hospitalization, or even surgery.

SUMMARY

In some aspects, a system is disclosed for gathering and processing sensor data to identify events that risk impacting an existing ulcer on a limb or risk causing a new ulcer on the limb. The system can include a memory device and a processor. The memory device can store sensor data collected by a first sensor configured to monitor movement or orientation of a user and a second sensor configured to monitor movement or orientation of an offloading device. The processor can: determine from a first set of the sensor data that a loading force was applied to a limb of the user which risked impacting an existing ulcer on the limb or risked causing a new ulcer on the limb; add a first event to a first list, the first event indicating that the loading force was applied to the limb; determine from a second set of the sensor data that (i) the loading force was not applied to the limb, (ii) the user engaged in an activity for more than a threshold duration of time, and (iii) the user was not wearing the offloading device; and add a second event to a second list, the second event indicating that (i) the loading force was not applied to the limb, (ii) the user engaged in the activity for more than the threshold duration of time, and (iii) the user was not wearing the offloading device.

The system of the preceding paragraph can include one or more of the following features: The processor can transmit the first list and a subset of the second list to a computing device via a computer network for presentation on a display. The first sensor can include a first accelerometer and a first magnetometer, and the second sensor can include a second accelerometer and a second magnetometer, the sensor data including sensor data from the first accelerometer, the second accelerometer, the first magnetometer, and the second magnetometer. The processor can: add the first event to the first list responsive to determining that the loading force was applied to the limb; and add the second event to the second list responsive to determining that (i) the loading force was not applied to the limb, (ii) the user engaged in an activity for more than the threshold duration of time, and (iii) the user was not wearing the offloading device. The processor can: compare an acceleration value of the first set of the sensor data to an acceleration threshold to determine that the loading force was applied to the limb; and compare an acceleration value of the second set of the sensor data to the acceleration threshold to determine that the loading force was not applied to the limb. The activity can include standing, walking, or driving a vehicle.

In some aspects, a non-transitory computer readable medium is disclosed that has an application stored thereon that when executed by a processor of an electronic device can cause the processor to: receive, via a computer network, sensor data collected by a first sensor configured to monitor movement or orientation of a user and a second sensor configured to monitor movement or orientation of an offloading device; determine from a first set of the sensor data that a loading force was applied to a limb of the user which risked impacting an existing ulcer on the limb or risked causing a new ulcer on the limb; add a first event to a first list, the first event indicating that the loading force was applied to the limb; determine from a second set of the sensor data that (i) the loading force was not applied to the limb, (ii) the user engaged in an activity for more than a threshold duration of time, and (iii) the user was not wearing the offloading device; and add a second event to a second list, the second event indicating that (i) the loading force was not applied to the limb, (ii) the user engaged in the activity for more than the threshold duration of time, and (iii) the user was not wearing the offloading device.

The non-transitory computer readable medium of the preceding paragraph can include one or more of the following features: The application when executed by the processor can cause the processor to transmit the first list and a subset of the second list to a computing device via the computer network. The first sensor can include a first accelerometer and a first magnetometer, and the second sensor can include a second accelerometer and a second magnetometer, the sensor data including sensor data from the first accelerometer, the second accelerometer, the first magnetometer, and the second magnetometer. The application when executed by the processor can cause the processor to: compare an acceleration value of the first set of the sensor data to an acceleration threshold to determine that the loading force was applied to the limb; and compare an acceleration value of the second set of the sensor data to the acceleration threshold to determine that the loading force was not applied to the limb. The acceleration threshold can be at least 18 $m/s^2$. The application when executed by the processor can cause the processor to add a time to the first list, the time indicating when, based at least on the first set of the sensor data, the limb experienced the loading force. The application when executed by the processor can cause the processor to add a duration to the first list, the duration indicating how long, based at least on the first set of the sensor data, the limb experienced the loading force. The activity can be other than the user laying down with the limb raised. The limb can be a leg. The computer network can be or include a cellular communications network. The first list and the second list can be the same list and identify a plurality of events which risked impacting the existing ulcer or risked causing the new ulcer, the plurality of events including the first event and the second event. The application when executed by the processor can cause the processor to compare acceleration values over a duration of activity to an acceleration threshold to determine that the user engaged in the activity for more than the threshold duration of time, the activity duration being indicated by the second set of the sensor data. The first set of the sensor data can correspond to first sensor data collected by the first sensor and the second sensor over a first time period, and the second set of the sensor data can correspond to second sensor data collected by the first sensor and the second sensor over a second time period non-overlapping with the first time period. The application when executed by the processor can cause the processor to: add the first event to the first list responsive to determining from the first set of the sensor data that the loading force was applied to the limb; add the second event to the second list responsive to determining from the second set of the sensor data that (i) the loading force was not applied to the limb, (ii) the user engaged in the activity for more than the threshold duration of time, and (iii) the user was not wearing the offloading device; determine from a third set of the sensor data that the loading force was applied to the limb which risked impacting the existing ulcer on the limb or risked causing the new ulcer on the limb, the third set of the sensor data being different from the first set of the sensor data; add a third event to the first list responsive to determining from the third set of the sensor data that the loading force was applied to the limb, the third event being different from the first event; determine from a fourth set of the sensor data that (i) the loading force was not applied to the limb, (ii) the user engaged in the activity for more than the threshold duration of time, and (iii) the user was not wearing the offloading device, the fourth set of the sensor data being different from the second set of the sensor data; and add a fourth event to the second list, the fourth event indicating that (i) the loading force was not applied to the limb, (ii) the user engaged in the activity for more than the threshold duration of time, and (iii) the user was not wearing the offloading device, the fourth event being different from the second event. The offloading device can distribute an applied force to the limb away from the existing ulcer on the limb when the offloading device is worn by the user. The offloading device can be a removable cast.

In some aspects, a method is disclosed. The method can include: receiving, via a computer network, sensor data collected by a first sensor configured to monitor movement or orientation of a user and a second sensor configured to monitor movement or orientation of an offloading device; determining, by a processor, from a first set of the sensor data that a loading force was applied to a limb of the user which risked impacting an existing ulcer on the limb or risked causing a new ulcer on the limb; adding, by the processor, a first event to a first list, the first event indicating that the loading force was applied to the limb; determining, by the processor, from a second set of the sensor data that (i) the loading force was not applied to the limb, (ii) the user engaged in an activity for more than a duration of time, and (iii) the user was not wearing the offloading device; and adding, by the processor, a second event to a second list, the second event indicating that (i) the loading force was not applied to the limb, (ii) the user engaged in the activity for more than the duration of time, and (iii) the user was not wearing the offloading device.

The method of the preceding paragraph can further include transmitting the first list and a subset of the second list to a computing device via the computer network for presentation on a display.

In some aspects, a system is disclosed for gathering and processing sensor data to identify a risk of impacting or causing a skin injury. The system can include computer-readable memory and one or more processors. The system can: obtain sensor feature data including a first set of feature data and a second set of feature data, the first set of feature data representing output of a user sensor configured to be worn on a limb of a user, the second set of feature data representing output of an offloading device sensor coupled to an offloading device that is configured to be worn on the limb; determine an activity classification using the first set of feature data and an activity classification model; determine an offloading usage classification using the first set of feature data, the second set of feature data, and an offloading usage model; generate display data representing at least one of the activity classification or the offloading usage classification; and transmit the display data to a computing device configured to present the display data.

The system of the preceding paragraph can include one or more of the following features: The activity classification model can determine a degree to which the first set of feature data corresponds to each of a plurality of different activity classifications. The offloading usage model can determine a degree to which motion or orientation of the user sensor corresponds to motion or orientation of the offloading device sensor. The skin injury can be a diabetic foot ulcer or a venous leg ulcer. The user sensor can include a first accelerometer and a first magnetometer, and the offloading device sensor can include a second accelerometer and a second magnetometer, the sensor feature data representing output from the first accelerometer, the second accelerometer, the first magnetometer, and the second magnetometer. The system can be further configured to: determine a subsequent activity classification using a third set of feature data and the activity classification model, the third set of feature data representing output of the user sensor; and determine from the activity classification and the subsequent activity classification that a change in an activity of the user has occurred. The system can be further configured to: determine a subsequent offloading usage classification using a third set of feature data, a fourth set of feature data, and the offloading usage model, wherein the third set of feature data represents output of the user sensor, and the fourth set of feature data represents output of the offloading device sensor; and determine from the offloading usage classification and the subsequent offloading usage classification that a change usage of the offloading device by the user has occurred. The system can be further configured to: generate activity model input data using the first set of feature data; generate activity classification model output data using the activity model input data and the activity classification model; and identify, from the activity classification model output data, a data element having a value that satisfies a classification criterion to determine the activity classification, the activity classification being associated with the data element. The plurality of different activity classifications can include a motion classification, a no motion with static weight classification, a no motion with variations in force classification, and a laying down classification. The activity classification model can include a decision tree, a neural network, or a support vector machine. The offloading device can be a removable cast. The activity classification model can include a first decision tree configured to assign the first set of feature data to one of a plurality of different activity classifications, and the offloading usage model can include a second decision tree configured to determine whether motion or orientation of the user sensor corresponds to motion or orientation of the offloading device sensor.

In some aspects, a computer-implemented method is disclosed for gathering and processing sensor data to identify a risk of impacting or causing a skin injury. The computer-implemented method can include: receiving, via a computer network, sensor feature data representing output of a user sensor configured to be worn on a limb of a user; generating, by one or more computer processors, activity classification model output data using the sensor feature data and an activity classification model; determining, by the one or more computer processors, an activity classification from the activity classification model output data; and transmitting, via the computer network, display data representing the activity classification to a computing device configured to present the display data.

The computer-implemented method of the preceding paragraph can include one or more of the following features: The activity classification model output data can represent likelihoods that the sensor feature data corresponds to each of a plurality of different activity classifications. The plurality of different activity classifications can include a first activity classification representing motion of the limb and a second activity classification representing no motion of the limb with weight loading the limb. The computer-implemented method can further include identifying, by the one or more computer processors, the risk of impacting or causing the skin injury, the skin injury being a diabetic foot ulcer or a venous leg ulcer. The determining the activity classification can include determining that the activity classification model output data indicates the sensor feature data likely corresponds to a third activity classification representing no motion with variations in force on the limb of the user. The determining includes determining that the activity classification model output data indicates the sensor feature data likely corresponds to a fourth activity classification representing that the user is lying down. The computer-implemented method can further include: determining, by the one or more computer processors, a subsequent activity classification using second sensor feature data and the activity classification model, the second sensor feature data representing output of the user sensor; and determining, by the one or more computer processors from the activity classification and the subsequent activity classification, that a change in activity of the user has occurred. The computer-implemented method can further include: receiving, via the computer network, second sensor feature data representing output of an offloading device sensor coupled to an offloading device that is configured to be worn on the limb; and determining, by the one or more computer processors, an offloading usage classification using the sensor feature data, the second sensor feature data, and an offloading usage model, wherein the offloading usage model is configured to determine a degree to which motion or orientation of the user sensor corresponds to motion or orientation of the offloading device sensor. The computer-implemented method can further include: receiving, via the computer network, second sensor feature data representing output of an offloading device sensor coupled to an offloading device that is configured to be worn on the limb; determining, by the one or more computer processors, a subsequent offloading usage classification using second sensor feature data and the offloading usage model, the second sensor feature data representing output of the offloading device sensor; and determining, by the one or more computer processors from the offloading usage classification and the subsequent offloading usage classification, that a change in usage of the offloading device by the user has occurred. The computer-implemented method can further include loading, by the one or more computer processors, the activity classification model, the activity classification model including a decision tree, a neural network, or a support vector machine. The computer-implemented method can further include loading, by the one or more computer processors, the activity classification model, the activity classification model including a decision tree configured to assign the sensor feature data to one of the plurality of different activity classifications.

In some aspects, a non-transitory computer readable medium is disclosed that has an application stored thereon for gathering and processing sensor data to identify a risk of impacting or causing a skin injury. The application, when executed by one or more processors of a computing device, can cause the computing device to: receive, via a computer network, sensor feature data representing output of a user sensor configured to be worn on a limb of a user; generate activity classification model output data using the sensor feature data and an activity classification model; determine an activity classification from the activity classification model output data; and transmit, via the computer network, display data representing the activity classification to a second computing device configured to present the display data.

The non-transitory computer readable medium of the preceding paragraph can include one or more of the following features: The activity classification model output data can represent likelihoods that the sensor feature data corresponds to each of a plurality of different activity classifications. The plurality of different activity classifications can include a first activity classification representing motion of the limb and a second activity classification representing no motion of the limb with weight loading the limb. The plurality of different activity classifications can include a third activity classification representing no motion of the limb with variations in force on the limb. The plurality of different activity classifications can include a third activity classification representing the user is lying down. The activity classification model can include a decision tree, a neural network, or a support vector machine. The activity classification model can include a decision tree configured to assign the sensor feature data to one of the plurality of different activity classifications. The application, when executed by the one or more computer processors, can cause the computing device to: determine a subsequent activity classification using second sensor feature data and the activity classification model, the second sensor feature data representing output of the user sensor; and determine from the activity classification and the subsequent activity classification that a change in an activity of the user has occurred. The application, when executed by the one or more computer processors, can cause the computing device to: receive, via the computer network, second sensor feature data representing output of an offloading device sensor coupled to an offloading device that is configured to be worn by the limb; and determine an offloading usage classification using the sensor feature data, the second sensor feature data, and an offloading usage model, wherein the offloading usage model is configured to determine a degree to which motion or orientation of the user sensor corresponds to motion or orientation of the offloading device sensor. The application, when executed by the one or more computer processors, can cause the computing device to: receive, via the computer network, second sensor feature data representing output of an offloading device sensor coupled to an offloading device that is configured to be worn by the limb; determine a subsequent offloading usage classification using second sensor feature data and the offloading usage model, the second sensor feature data representing output of the offloading device sensor; and determine from the offloading usage classification and the subsequent offloading usage classification that a change in usage of the offloading device by the user has occurred.

In some aspects, a system is disclosed for gathering and processing sensor data to identify a risk of impacting or causing a skin injury. The system can include computer-readable memory and one or more processors. The system can: obtain sensor feature data including a first set of feature data and a second set of feature data, the first set of feature data representing output of a user sensor configured to be worn on a limb of a user, the second set of feature data representing output of an offloading device sensor coupled to an offloading device that is configured to be worn on the limb; determine an activity classification using the first set of feature data and an activity classification model, wherein the activity classification model can include a first decision tree configured to assign the first set of feature data to one of a plurality of different activity classifications; determine an offloading usage classification using the first set of feature data, the second set of feature data, and an offloading usage model, wherein the offloading usage model can include a second decision tree configured to determine whether motion or orientation of the user sensor corresponds to motion or orientation of the offloading device sensor; generate display data representing at least one of the activity classification or the offloading usage classification; and transmit the display data to a computing device configured to present the display data.

In some aspects, a system is disclosed for gathering and processing sensor data to identify a risk of impacting or causing a skin injury. The system can include computer-readable memory and one or more processors. The system can: obtain sensor feature data including a set of feature data representing output of a user sensor configured to be worn on a limb of a user; determine an activity classification using the set of feature data and an activity classification model, wherein the activity classification model can include a decision tree configured to assign the set of feature data to one of a plurality of different activity classifications; generate display data representing the activity classification; and transmit the display data to a computing device configured to present the display data.

BRIEF DESCRIPTION OF THE DRAWINGS

Embodiments of the present disclosure will now be described hereinafter, by way of example only, with reference to the accompanying drawings in which.

DETAILED DESCRIPTION

Introduction to User Activity Monitoring

Figure 1:
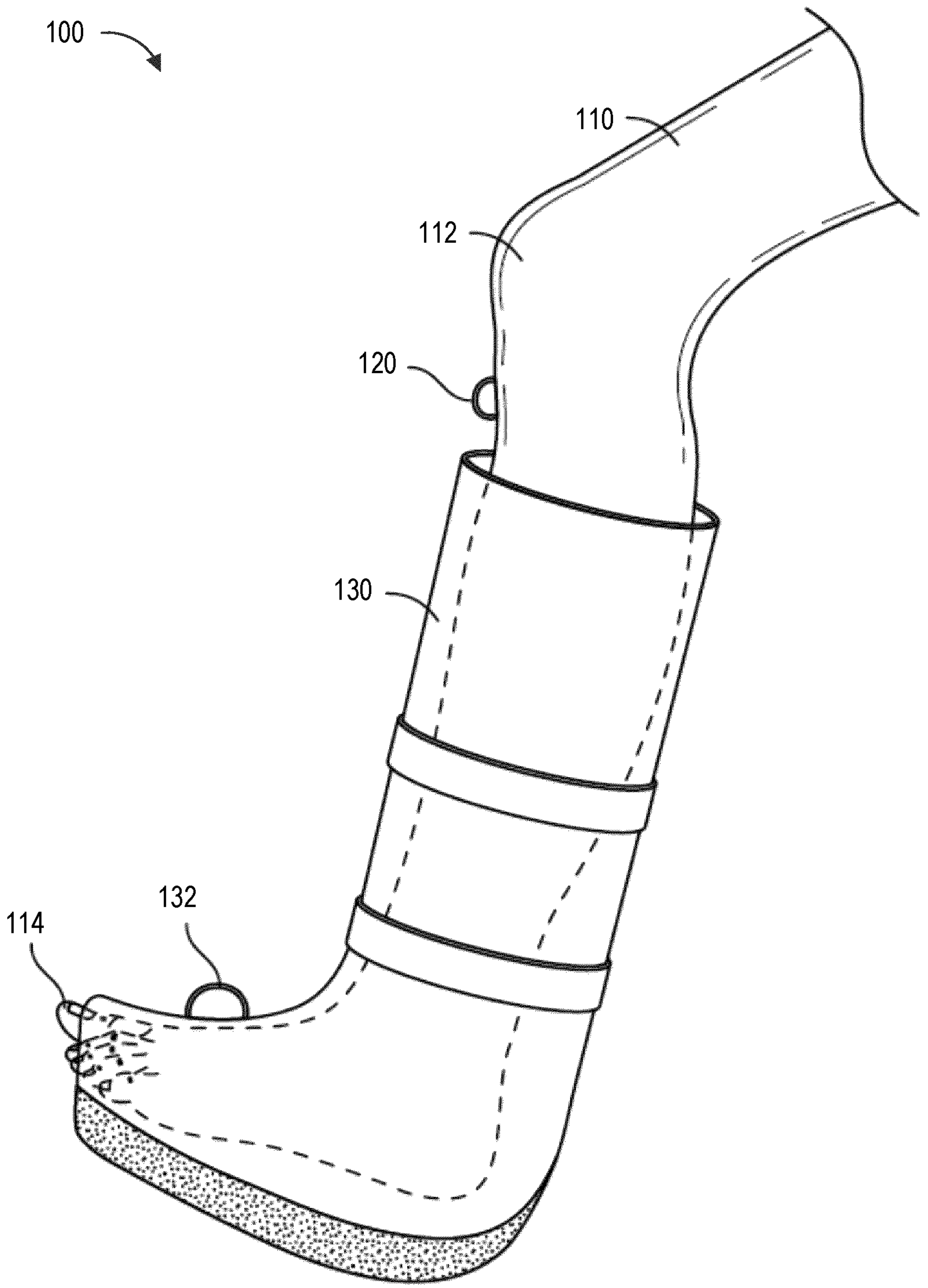
FIG. 1 illustrates an example user activity monitoring system that includes an activity monitoring device and an offloading monitoring device.

Activities of a user may be desirably monitored by an activity monitoring device for a variety of reasons, including wound prevention and monitoring. In one example, the activities of a user can be monitored when the user may be prone to or already have a wound, such as a pressure ulcer. Information gathered by the activity monitoring device about the activities of the user can be helpful for assisting with prevention or treatment of the pressure ulcer. In addition, information gathered by the activity monitoring device about the activities can be useful for checking compliance with a treatment regimen.

Some aspects disclosed herein relate to wound monitoring or therapy for a human or animal body. Therefore, any reference to a wound herein can refer to a wound on a human or animal body, and any reference to a body herein can refer to a human or animal body. The disclosed technology may relate to preventing or minimizing damage to physiological tissue or living tissue, or to the treatment of damaged tissue (for example, a wound as described herein).

As used herein the expression "wound" may include an injury to living tissue that may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound can become a chronic wound when it does not follow the healing stages resulting in a lengthened recovery. It is believed that the transition from acute to chronic wound can be due to a patient being immuno-compromised.

Chronic wounds may include for example: venous ulcers (such as those that occur in the legs), which account for the majority of chronic wounds and mostly affect the elderly, diabetic ulcers (for example, foot or ankle ulcers), peripheral arterial disease, pressure ulcers, or epidermolysis bullosa (EB).

Examples of other wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Wounds may include a deep tissue injury. Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

Wound may also include tissue at risk of becoming a wound as discussed herein. For example, tissue at risk may include tissue over a bony protuberance (at risk of deep tissue injury/insult) or pre-surgical tissue (for example, knee tissue) that may have the potential to be cut (for example, for joint replacement/surgical alteration/reconstruction).

Some aspects relate to methods of monitoring or treating a wound with the technology disclosed herein in conjunction with one or more of the following: advanced footwear, turning a patient, offloading (such as, offloading diabetic foot ulcers), treatment of infection, systemix, antimicrobial, antibiotics, surgery, removal of tissue, affecting blood flow, physiotherapy, exercise, bathing, nutrition, hydration, nerve stimulation, ultrasound, electrostimulation, oxygen therapy, microwave therapy, active agents ozone, antibiotics, antimicrobials, or the like.

Alternatively or additionally, a wound may be treated using topical negative pressure or traditional advanced wound care, which is not aided by the using of applied negative pressure (may also be referred to as non-negative pressure therapy).

Although the present disclosure may refer to pressure ulcers, foot ulcers, or the like, the systems and methods disclosed herein can be used for preventing, monitoring, or treating any type of skin injury or wound, such as a venous leg ulcer.

User Activity Monitoring System

FIG. 1 illustrates a user activity monitoring system 100 including an activity monitoring device 120 attached to a body part 110. The activity monitoring device 120 can be attached to the body part 110 using a strap, adhesive, or other coupling mechanism and may be worn on or supported by the body.

The body part 110 can be a limb of a user, such as a leg that includes a knee 112 and a foot 114. As illustrated, the activity monitoring device 120 can be supported by the body part 110 at a position between the knee 112 and the foot 114, such as proximate to the knee 112. In other aspects, the activity monitoring device 120 can be supported by another part of the body part 110, such as above the knee 112 or elsewhere. The activity monitoring device 120 can monitor and record activities (for instance, walking, jumping, sitting, laying down, running, squatting, or standing) of the body part 110, such as from a position, movement, or orientation of the activity monitoring device 120 or one or more other sensors of the activity monitoring device 120. The activity monitoring device 120 can, for example, be used for loading monitoring of loading of the foot 114. In certain implementations, multiple body parts can be monitored by the activity monitoring device 120, and different sensors can be used for monitoring different body parts. Individual sensors of or in communication with the activity monitoring device 120 may be referred to as user sensors, or sometimes as user motion sensors.

The body part 110 is shown wearing and being partly covered by an offloading device 130, such as a removable cast. The offloading device 130 can support the body part 110 and reduce a pressure on the foot 114 when the user may be standing or engaging in other activities. The offloading device 130 can distribute an applied force to the body part 110 away from an injury when the offloading device is worn. An offloading monitoring device 132 can be attached to the offloading device 130. The offloading monitoring device 132 can be the same as or similar to the activity monitoring device 120 and monitor and record activities of the offloading device 130. The offloading monitoring device 132 can be supported by the offloading device 130 using a strap, adhesive, or other coupling mechanism. The offloading monitoring device 132 can be attached to an inner surface or outer surface of the offloading device 130. Although not shown in FIG. 1, the offloading monitoring device 132 may be attached to an offloading device that is not worn by the user (for example, a cane or a walker). Moreover, the activity monitoring device 120 can be worn regardless of whether the offloading device 130 may be worn. Individual sensors of or in communication with the offloading monitoring device 132 may be referred to as offloading device sensors, or sometimes as offloading device motion sensors.

The user activity monitoring system 100 can additionally or alternatively include one or more of the activity monitoring device 120 or the offloading monitoring device 132 at other positions, such as at a position supported by the offloading device 130, another part of the body part 110, another device not worn such as a cane or a walker, or elsewhere. The one or more additional or alternative of the activity monitoring device 120 or the offloading monitoring device 132 can be the same as or similar to the activity monitoring device 120 may monitor and record activities of the offloading device 130, the another part of the body part 110, or the body.

Figure 2:
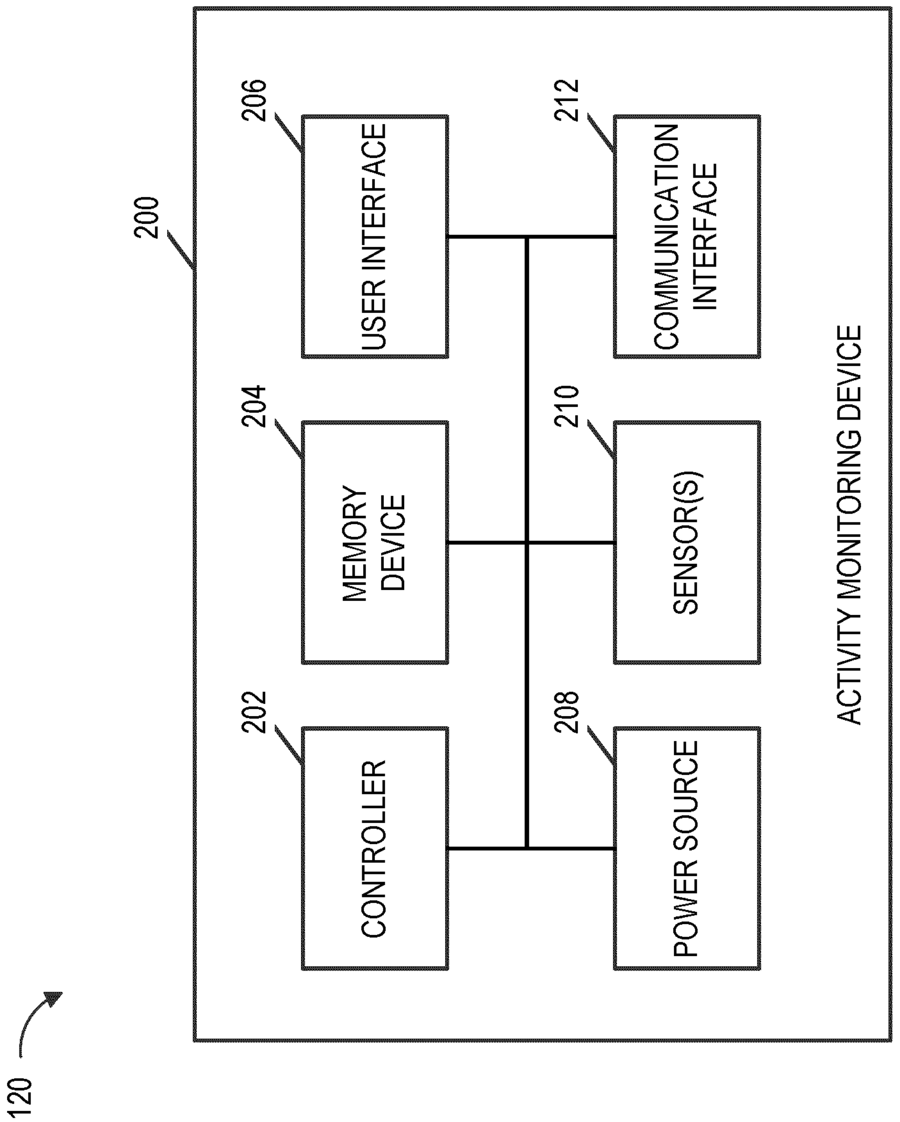
FIG. 2 illustrates example components of the activity monitoring device of FIG. 1.

FIG. 2 illustrates example components of the activity monitoring device 120. The activity monitoring device 120 can include a housing 200, a controller 202, a memory device 204, a user interface 206, a power source 208, one or more sensors 210, and a communication interface 212 that are configured to communicate, such as electrically, with one another. The power source 208 can provide power to one or more components of the activity monitoring device 120.

One or more of the components of the activity monitoring device 120 can be contained in or supported by the housing 200. The housing 200 can be composed of a top portion and a bottom portion that are sealed together, and the top portion or the bottom portion can be hard or soft. The housing 200 can be flexible and have a mechanical structure and design features that provide for a shouldered keyway alignment of components within the housing 200. The housing 200 can support a circuit board on its inside and on which one or more components of the activity monitoring device 120 may be positioned.

The housing 200 can be made by stereolithography (SLA) or polyjet from photopolymer 3D printing material or by 3D printing from an engineering resin with a shorehardness of 80 A. The housing 200 can include an elastomer, a thermoplastic elastomer, or be constructed by injection molding. The molded parts of the housing 200 can be made from liquid silicone rubber in white. An adhesive (for example, one for attaching plastics and elastomeric materials) can be used to glue the top and bottom portions of the housing 200 together, and a wide range of other adhesives (for example, cyanoacrylates, silicones, epoxies, hydrogels, hydrocolloids, sealant systems) or other techniques (for example use of double-sided adhesive tapes, ultrasonic welding, staking) can be used.

The controller 202 can control operations of one or more other components (for instance, the memory device 204, the user interface 206, the power source 208, the one or more sensors 210, or the communication interface 212) of the activity monitoring device 120 according at least to instructions stored in the memory device 204. The controller 202 can, for instance, control monitoring of loading of the body part 110 with a weight of the body or positioning of the body part 110 and record data indicative of loading of the body part 110 or positioning of the body part 110 to the memory device 204.

The user interface 206 can include one or more output elements, such as visual feedback devices (for example, light emitting diodes), haptic feedback devices, or audio devices (for example, speakers), that provide user outputs to a user. The one or more output elements can convey status information to the user like whether the activity monitoring device 120 is successfully functioning or has successfully configured communication with another device. The user interface 206 can include one or more input elements, such as buttons, switches, dials, touch pads, microphones, or touch screens, for receiving user inputs for configuring the activity monitoring device 120. In some aspects, the user interface 206 may have no more than one user input element, such as a button, for receiving user inputs to activate and deactivate the activity monitoring device 120 or performing one or more other functions.

The one or more sensors 210 can be used to detect and monitor a motion or an orientation of the activity monitoring device 120 or other characteristics of or around the activity monitoring device 120. The one or more sensors 210 can be used to detect and monitor activities of the user of the activity monitoring device 120 that include, for instance, a loading or positioning of the body part 110. The one or more sensors 210 can include one or more accelerometers, gyroscopes, magnetometers, impedance sensors, thermistors, pressure sensors, or optical sensors, among other types of sensors. The one or more sensors 210 can be positioned by the housing proximate to the body part 110 or may be remote from the body part 110 yet usable to monitor characteristics of the body part 110.

The controller 202 and the one or more sensors 210 can be used to determine multiple features indicative of movement by or orientation of the activity monitoring device 120 over a data window. For example, the controller 202 can use an accelerometer (which senses x-axis, y-axis, and z-axis acceleration) and a magnetometer (which senses x-axis, y-axis, and z-axis magnetic field variation) of the one or more sensors 210 to determine one or more or all of the data features listed in Table 1, including for individual data windows, such as over time periods of 1, 2, 5, 10, 20, or 30 seconds. The data features determined from accelerometer data can include "Acc" in their names, and the data features determined from magnetometer data can include "Mag" in their names.

TABLE 1

| Data Feature | Description |
|---|---|
| tBodyMag_correlationXZ | Correlation of Magnetometer X and Z |
| tBodyMag_correlationXY | Correlation of Magnetometer X and Y |
| tBodyAccX_mean | Mean of Accelerometer X |
| tBodyAcc_mag_iqr | IQR of Magnitude of Accelerometer X, Y, and Z |
| tBodyMagY_energy | Energy of Magnetometer Y |
| tBodyMag_correlationYZ | Correlation of Magnetometer Y and Z |
| tBodyMagY_mean | Mean of Magnetometer Y |
| tBodyAcc_sma | Signal magnitude area of the Accelerometer |
| tBodyMagX_mean | Mean of Magnetometer X |
| tBodyMag_mag | Magnitude of the Magnetometer X, Y, and Z |
| tBodyAcc_correlationXY | Correlation of Accelerometer X and Y |
| tBodyMag_sma | Signal magnitude area of the Magnetometer |
| tBodyMagZ_mean | Mean of Magnetometer Z |
| tBodyAccZ_mean | Mean of Accelerometer Z |

TABLE 1-continued

| Data Feature | Description |
|---|---|
| tBodyAccZ_energy | Energy of Accelerometer Z |
| tBodyAcc_mag | Magnitude of the Magnetometer X, Y, and Z |
| tBodyAcc_correlationYZ | Correlation of Accelerometer Y and Z |
| tBodyAccY_mean | Mean of Accelerometer Y |
| tBodyAccZ_min | Minimum of Accelerometer Z |
| tBodyAccY_min | Minimum of Accelerometer Y |
| tBodyAccX_iqr | IQR of Accelerometer X |
| tBodyAcc_correlationXZ | Correlation of Accelerometer X and Z |
| tBodyAccX_std | Standard Deviation of Accelerometer X |
| tBodyMagZ_energy | Energy of Magnetometer Z |
| tGravityAccX_iqr | IQR of Accelerometer X in the Gravity Acceleration space |
| tBodyAccX_max | Maximum of Accelerometer X |
| tGravityAcc_sma | Signal Magnitude Area of Accelerometer in the Gravity Acceleration space |
| tBodyMagX_energy | Energy of Magnetometer X |
| tBodyAccZ_mad | Mean Absolute Deviation |
| tGravity_vector | Vector for Gravity Reference |

The data features in Table 1 can, for example, be calculated at least according to equations provided in Table 2.

TABLE 2

| Reference | Equation |
|---|---|
| Mean (first moment) | $\bar{x} = \frac{1}{N}\sum_i x_i$ |
| Standard Deviation (second moment) | $s = \frac{1}{N}\sqrt{\sum_i (x_i - \bar{x})^2}$ |
| Median | Middle value of sorted $x_i$ or at n/2 |
| Minimum | Smallest value of $x_i$ |
| Maximum | Largest value of $x_i$ |
| Skewness (third moment) | $\frac{\frac{1}{N}\sqrt{\sum_i (x_i - \bar{x})^3}}{s^3}$ |
| Kurtosis (fourth moment) | $\frac{\frac{1}{N}\sqrt{\sum_i (x_i - \bar{x})^4}}{s^4}$ |
| Energy | $\frac{1}{N}\sum_i (x_i \cdot x_i)$ |
| Interquartile Range (IQR) | Sort $x_i$ then subtract the median of the upper half and lower half |
| Signal Magnitude Area | $\sum_i (x_i + y_i + z_i)$ |
| Correlation between $x_i$ and $y_i$ | $\sum_i (x_i \cdot y_i)$ |
| Correlation between $x_i$ and $z_i$ | $\sum_i (x_i \cdot z)$ |
| Correlation between $y_i$ and $z_i$ | $\sum_i (z_i \cdot z_i)$ |
| Magnitude of triad | $\sum_i \sqrt{x_i \cdot x_i + y_i \cdot y_i + z_i \cdot z_i}$ |

The data feature of tGravity_vector in Table 1 can be indicative of a relative direction of gravity for the activity monitoring device 120 when the body part 110 may be vertical, such as when the user of the activity monitoring device 120 is standing. The data feature of tGravity_vector can be used to account for the placement or orientation of the housing 200 with respect to the body part 110 (as well as potential variations in size or shape of the body part 110) without having a calibration step for the activity monitoring device 120 that ensures a particular placement or orientation of the housing 200 with respect to gravity. The data feature of tGravity_vector can be calculated from multiple detected gravity vectors by the one or more sensors 210 over time, such as periodically (for instance, every 0.2, 0.5, 1, 2, or 5 seconds) from an average (for instance, a running average of past 2, 5, 10, 20, 50, 200, or 500 vectors) of the multiple detected gravity vectors while the user may be determined to be walking (for instance, the user can be determined to be walking by the controller 202 from detection of one or more steps or a high acceleration using the one or more sensors 210). The value of the data feature of tGravity_vector can reset upon a change in position of the activity monitoring device 120 relative to the body part 110, such as a detachment of the activity monitoring device 120 from the body part 110.

Tables 3 and 4 together illustrate example calculations of the data feature of tGravity_vector. Table 3 includes 20 example data samples, including the x, y, and z components of one detected gravity vector for each sample and one indication for each sample of whether the user was walking at the time of the sample.

TABLE 3

| Sample | x | y | z | Walking? |
|---|---|---|---|---|
| 1 | −0.512 | −1.100 | 0.150 | No |
| 2 | −0.100 | −0.900 | 0.170 | No |
| 3 | −0.320 | −0.800 | 0.120 | No |
| 4 | −0.660 | −0.910 | 0.150 | No |
| 5 | −0.830 | −0.750 | 0.150 | No |
| 6 | −0.512 | −1.020 | 0.170 | Yes |
| 7 | 0.100 | −0.900 | 0.120 | Yes |
| 8 | −0.320 | −0.800 | 0.150 | Yes |
| 9 | −0.660 | −0.910 | 0.150 | Yes |
| 10 | −0.200 | −0.750 | 0.170 | Yes |
| 11 | −0.200 | −1.020 | 0.120 | Yes |
| 12 | −0.100 | −0.800 | 0.150 | Yes |
| 13 | −0.320 | −0.910 | 0.150 | No |
| 14 | −0.660 | −0.750 | 0.170 | No |
| 15 | −0.830 | −1.020 | 0.120 | No |
| 16 | −0.512 | −0.900 | 0.150 | No |
| 17 | −0.100 | −0.800 | 0.150 | No |
| 18 | −0.320 | −0.910 | 0.170 | No |
| 19 | −0.660 | −0.800 | 0.120 | Yes |
| 20 | −0.830 | −0.910 | 0.150 | Yes |

Table 4 includes example values of tGravity_vector for the 20 data samples of Table 3. The calculation of tGravity_vector, which can include components GVx, GVy, and GVz, can be initialized with a starting or default vector, such as <x=−0.353, y=−0.928, z=0.121>. The SUM(X), SUM (Y), and SUM(Z) columns can provide a running summation, including the starting or default vector, across the samples of the x, y, and z components of one detected gravity vector for each sample where the one indication denotes that the user was walking at the time of the sample. The WCount column can be initialized to one and provide a running summation of a number of samples during which the user was walking at the time of the sample. The GVx, GVy, and GVz columns can provide the calculated values for tGravity_vector, which can be the values of the SUM(X), SUM(Y), and SUM(Z) columns divided by the respective value of the WCount column. As can be seen, the value of tGravity_vector can accordingly be updated when the user may be walking but not when the user may not be walking.

TABLE 4

| Sample | SUM (x) | SUM (y) | SUM (z) | WCount | GVx | GVy | GVz |
|---|---|---|---|---|---|---|---|
| 1 | −0.353 | −0.928 | 0.121 | 1 | −0.353 | −0.928 | 0.121 |
| 2 | −0.353 | −0.928 | 0.121 | 1 | −0.353 | −0.928 | 0.121 |
| 3 | −0.353 | −0.928 | 0.121 | 1 | −0.353 | −0.928 | 0.121 |
| 4 | −0.353 | −0.928 | 0.121 | 1 | −0.353 | −0.928 | 0.121 |
| 5 | −0.353 | −0.928 | 0.121 | 1 | −0.353 | −0.928 | 0.121 |
| 6 | −0.865 | −1.948 | 0.291 | 2 | −0.433 | −0.974 | 0.146 |
| 7 | −0.765 | −2.848 | 0.411 | 3 | −0.255 | −0.949 | 0.137 |
| 8 | −1.085 | −3.648 | 0.561 | 4 | −0.271 | −0.912 | 0.140 |
| 9 | −1.745 | −4.558 | 0.711 | 5 | −0.349 | −0.912 | 0.142 |
| 10 | −1.945 | −5.308 | 0.881 | 6 | −0.324 | −0.885 | 0.147 |
| 11 | −2.145 | −6.328 | 1.001 | 7 | −0.306 | −0.904 | 0.143 |
| 12 | −2.245 | −7.128 | 1.151 | 8 | −0.281 | −0.891 | 0.144 |
| 13 | −2.245 | −7.128 | 1.151 | 8 | −0.281 | −0.891 | 0.144 |
| 14 | −2.245 | −7.128 | 1.151 | 8 | −0.281 | −0.891 | 0.144 |
| 15 | −2.245 | −7.128 | 1.151 | 8 | −0.281 | −0.891 | 0.144 |
| 16 | −2.245 | −7.128 | 1.151 | 8 | −0.281 | −0.891 | 0.144 |
| 17 | −2.245 | −7.128 | 1.151 | 8 | −0.281 | −0.891 | 0.144 |
| 18 | −2.245 | −7.128 | 1.151 | 8 | −0.281 | −0.891 | 0.144 |
| 19 | −2.905 | −7.928 | 1.271 | 9 | −0.323 | −0.881 | 0.141 |
| 20 | −3.735 | −8.838 | 1.421 | 10 | −0.374 | −0.884 | 0.142 |

The controller 202 and the one or more sensors 210 can, for example, operate under or calculate data features according to one or more of the data collection or processing settings listed in Table 5.

TABLE 5

| Setting | Value |
|---|---|
| TIMEOUT_1 | 10 minutes |
| $T_0$ | Current Time |
| ACCEL_COLLECT_FREQUENCY | 50 Hz |
| MAG_COLLECT_FREQUENCY | 25 Hz |
| BUFFER_PERIOD | 5 s |
| Y_PERIOD | 1 s |
| Y_FORMAT | 16 bit float |
| X_PERIOD | 1 s |
| X_FORMAT | 16 bit float |
| RMS_Y_PERIOD | 1 s |
| RMS_Y_FORMAT | 16 bit float |
| SHOCK_FORMAT | 32 bit timestamp, 16 bit acceleration value |
| WINDOW SIZE | 500 data points |
| WINDOW OVERLAP | 0 data points |

The settings listed in Table 5 can advantageously, in certain aspects, permit the activity monitoring device 120 to operate for at least 7 days, which may mean that the memory device 204 and the power source 208 can continue to operate without failing (such as due to memory overflow or insufficient power) for at least 7 days. The activity monitoring device 120 can be designed or constructed, in some aspects, to not last much longer than 7 days. For example, the activity monitoring device 120 can operate such that the memory device 204 overflows after 10, 12, 14, 16, 18, 20, 22, or 24 days. As another example, the activity monitoring device 120 can operate such that the power source can be expected to fail after 10, 12, 14, 16, 18, 20, 22, or 24 days. In some implementations, the activity monitoring device 120 can be designed or constructed to operate for less or more than 7 days, such as for 5 days, 10 days, 12 days, or the like.

The data features listed in Table 1 can desirably, in some aspects, be processed by the controller 202 despite the controller 202 having processing limitations, such as a limited data sorting ability. Because the activity monitoring device 120 may be portable and designed to have a compact size or form, the controller 202 may be selected to have a compact size or form that may as a result have fewer processing features or computational abilities than some other controllers. Moreover, the data features listed in Table 1 may have been selected from among additional data features because the data features of listed in Table 1 may be together usable for accurately (for instance, with around 90% or 95% confidence) detecting a high acceleration experienced by the activity monitoring device 120, classifying an activity engaged in by a user wearing the activity monitoring device 120, or detecting an offloading device usage by the user wearing the activity monitoring device 120. Fewer than all of the data features listed in Table 1 (or alternative features) may be used, in some instances, if a lower detection accuracy may be acceptable.

The controller 202 can store without loss or with loss of precision (such as losslessly or lossy) the determinations of the data features in the memory device 204. A lossless storage approach can advantageously, in certain aspects, ensure that the data feature determinations are continuously monitored and recorded once the activity monitoring device 120 begins monitoring and recording and throughout use of the activity monitoring device 120. The controller 202 may or may not store raw sensor data, such as x-axis accelerometer data or z-axis magnetometer data, to the memory device 204. The controller 202 may not, in some aspects, store the raw sensor data to the memory device 204 at least to limit a utilization of the memory device 204 and permit the memory device 204 to be selected to have a lower memory capacity than may be otherwise used.

The communication interface 212 can be used to communicate with other devices, such as wirelessly via radio waves. The communication can be performed according to a communication protocol, such as a Bluetooth™ protocol like Bluetooth™ Low Energy. The communication interface 212 can, for example, communicate and pair with other devices and transmit device usage or sensor data (such as [i] sensor-derived data including the determined values of one or more of the data features listed in Table 1 over data windows, [ii] monitored loading or positioning, [iii] alarms, or [iv] changes to a monitoring or therapy program performed by the activity monitoring device 120) to the other devices. The communication interface 212 can be used to receive data, including commands, from the other devices. The communication interface 212 can permit communication with (for example, transfer of data to or processing commands from) another device once a communication channel has been configured for communication with the another device (for example, by device pairing). The communication interface 212 may, in some aspects, be unable to communicate farther than 10 meters, 30 meters, or 100 meters away from the communication interface 212.

Figure 3:
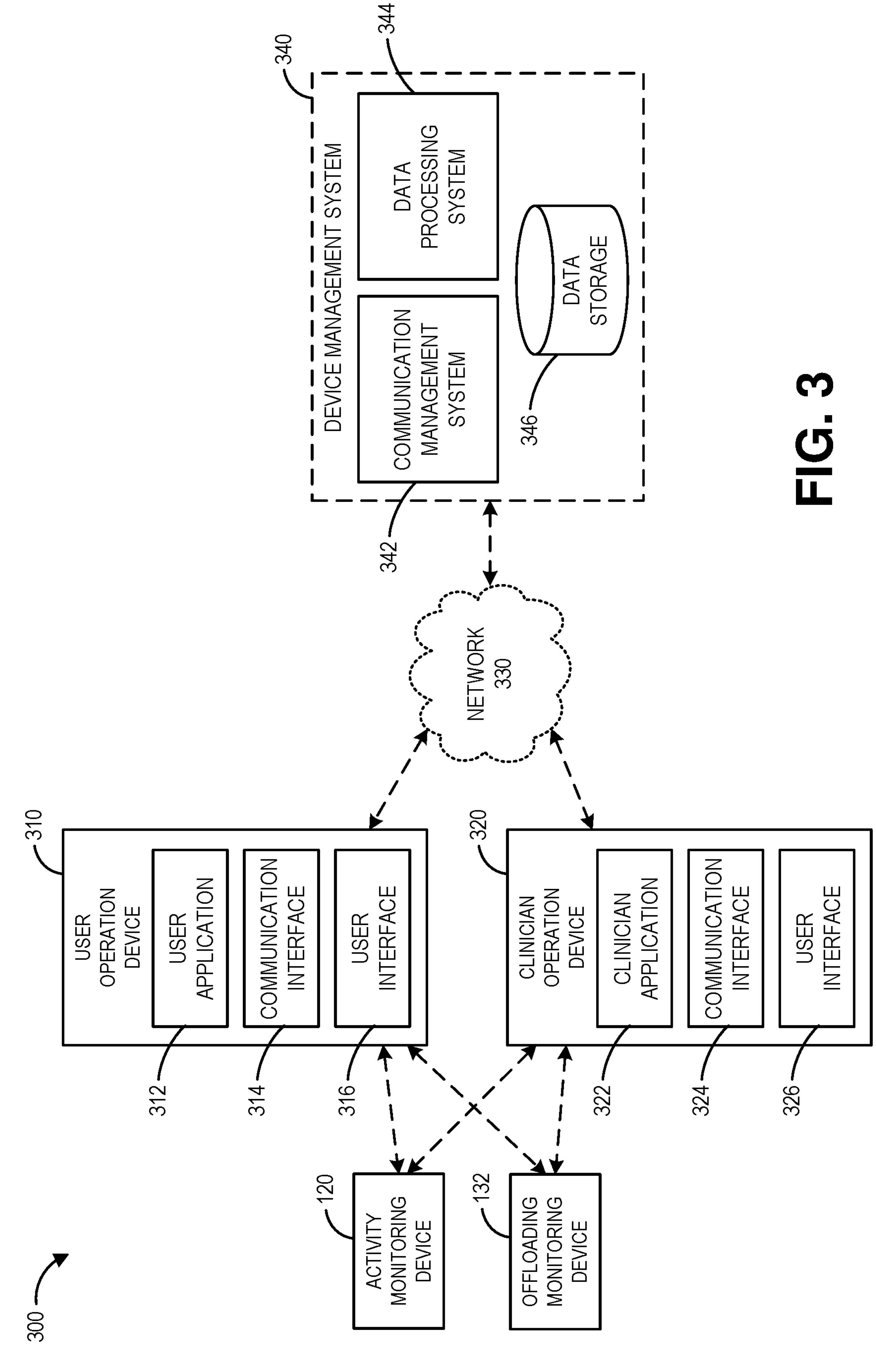
FIG. 3 illustrates an example computing environment that includes the activity monitoring device and the offloading monitoring device of FIG. 1.

FIG. 3 illustrates a computing environment 300 that includes the activity monitoring device 120 and the offloading monitoring device 132. The computing environment 300 shows the activity monitoring device 120 and the offloading monitoring device 132 in communication with a user operation device 310 and a clinician operation device 320, as well as the user operation device 310 and the clinician operation device 320 in communication with a device management system 340 via a network 330.

The user operation device 310 can be operated by a user, such as a wearer, of the activity monitoring device 120 and the offloading monitoring device 132. The user operation device 310 can permit the user to use the user operation device 310 to collect, process, review, or transmit the data gathered by the activity monitoring device 120 and the offloading monitoring device 132. On the other hand, the clinician operation device 320 can be operated by a clinician for the user, such as an individual who supervises, assists, or cares for the user that uses the activity monitoring device 120 and the offloading monitoring device 132. The clinician operation device 320 can permit the clinician to use the clinician operation device 320 to collect, process, review, or transmit the data gathered by the activity monitoring device 120 and the offloading monitoring device 132.

The user operation device 310 and the clinician operating device 320 may each be a computing device such as a smart phone, a tablet computer, or a desktop computer. In some aspects, the user operation device 310 and the clinician operating device 320 can receive, send, present, and access data gathered by the activity monitoring device 120 and the offloading monitoring device 132 or data determined therefrom, but may not process the data gathered by the activity monitoring device 120 and the offloading monitoring device 132 to analyze the characteristics of the data (such as to identify from the data when the user used an offloading device or calculate a duration of activity engaged in by the user).

The user operation device 310 can include a user application 312, a communication interface 314 (which can, for instance, include any one or more of the features of the communication interface 212), and a user interface 316 (which can, for instance, include any one or more of the features of the user interface 206). The user application 312 can be a program that is executed by a processor of the user operation device 310. The user application 312 can enable the user operation device 310 to communicate via the communication interface 314 with the activity monitoring device 120, the offloading monitoring device 132, and the device management system 340. The user application 312 may receive, collect, process, review, or transmit (i) data gathered or determined by the activity monitoring device 120 and the offloading monitoring device 132, such as determined feature data, sensor data, alarms, monitored loading or positioning, or changes to a monitoring or therapy program, (ii) data collected or determined by the user application 312, such as user observations, goal information, or identifications of activities engaged in by a user, or (iii) data collected or determined by the device management system 340, such as a duration of time that the user was active, a portion of time that the user used an offloading device, or an amount of time at which an injury of the user may be at risk due to activity by the user or nonuse of the offloading device. The user application 312 can moreover present to the user one or more graphical user interfaces with the user interface 316, such as on a display or a touchscreen of the user interface 316.

The user application 312 can be used to gather information from the user to assist with understanding what type of activity was engaged in by the user when the foot of the user may have experienced a loading force which risked adversely impacting an existing ulcer on the foot or risked causing a new ulcer on the foot. The user application 312 can receive from the device management system 340 a time that the sensor data from the activity monitoring device 120 indicates a foot of the user experienced a loading force which risked adversely impacting an existing ulcer on the foot or risked causing a new ulcer on the foot, and the user application 312 can determine a geographic location of the user operation device 310 (such as from a global positioning system (GPS) receiver of the user operation device 310 or a communication received by the user operation device 310 via the network 330) that may be indicative of a geographic location of the activity monitoring device 120 at the time. The user application 312 may output the time and the geographic location of the user operation device 310 along with a request that the user identify the type of activity engaged in by the user at the time and the geographic location. The type of activity can, for example, include a type of transportation, a type of exercise, a type of leisure, a type of hobby, or a type of work. The request may list a set of types of activities commonly engaged in by the user to assist in selecting the type of activity engaged in by the user.

The user application 312 can include features and interfaces that seek to increase the amount or frequency of user engagement with the user application 312. The user application 312 may request contextual information (such as an identification of an activity engaged in by the user while wearing the activity monitoring device 120 or an indication by the user of how the user is feeling) to assist with tracking or understanding why the foot of the user may have experienced a loading force which risked adversely impacting an existing ulcer on the foot or risked causing a new ulcer on the foot.

The clinician operation device 320 can include a clinician application 322, a communication interface 324 (which can, for instance, include any one or more of the features of the communication interface 212), and a user interface 326 (which can, for instance, include any one or more of the features of the user interface 206). The clinician application 322 can be a program that is executed by a processor of the clinician operation device 320. The clinician application 322 can enable the clinician operation device 320 to communicate via the communication interface 324 with the activity monitoring device 120, the offloading monitoring device 132, and the device management system 340. The clinician application 322 may receive, collect, process, review, or transmit (i) data gathered or determined by the activity monitoring device 120 and the offloading monitoring device 132, such as determined feature data, sensor data, alarms, monitored loading or positioning, or changes to a monitoring or therapy program, (ii) data collected or determined by the user application 312, such as user observations, goal information, or identifications of activities engaged in by a user, or (iii) data collected or determined by the device management system 340, such as a duration of time that the user was active, a portion of time that the user used an offloading device, or an amount of time at which an injury of the user may be at risk due to activity by the user or nonuse of the offloading device. The clinician application 322 can present to the clinician one or more graphical user interfaces with the user interface 326, such as on a display or a touchscreen of the user interface 326.

In some aspects, the clinician operation device 320 may not directly communicate with the activity monitoring device 120 or the offloading monitoring device 132. Instead, the clinician operation device 320 may receive any data collected by or associated with the activity monitoring device 120 and offloading monitoring device 132 from the device management system 340. Such a design may desirably limit the number of devices (other than the user operation device 310) that may receive data directly from the activity monitoring device 120 and the offloading monitoring device 132 and thereby enhance the security of and limit access to the data.

The device management system 340 can be a computing device, such as a server, and include a communication management system 342, a data processing system 344, and a data storage 346 that may be in communication with one another. The device management system 340 may, for instance, be constructed partly or entirely of a server infrastructure or a cloud architecture, such as using a cloud infrastructure provided by Amazon Web Services™ (AWS), Microsoft™ Azure™, Google Cloud Platform™ (GCP), or Oracle™ Cloud Infrastructure (OCI). The server infrastructure and the cloud infrastructure can be compliant with the requirements of HIPAA (Health Insurance Portability and Accountability Act of 1996) and provide data privacy and security protections in view of the potentially sensitive nature of the data collected, processed, or determined by the device management system 340.

The communication management system 342 may permit the device management system 340 to communicate over the network 330 with the user operation device 310 and the clinician operation device 320. The communication management system 342 can include an application programming interface (API), such as a cloud API, to facilitate its communications.

The data processing system 344 can collect, process, present, store (such as in the data storage 346), or transmit the data gathered or determined by the activity monitoring device 120 and the offloading monitoring device 132 (such as determined feature data, sensor data, alarms, monitored loading or positioning, or changes to a monitoring or therapy program) and the data collected or determined by the user application 312 (such as user observations, goal information, or identifications of activities engaged in by a user). For example, the data processing system 344 can process the data gathered by the activity monitoring device 120 and the offloading monitoring device 132 to determine an activity likely engaged in by the user during various periods of time over which the data was gathered, as well as whether the user likely wore an offloading device during various periods of time over which the data was gathered. The determined likely activity or use of the offloading device may be shared by the device management system 340 with the user operation device 310 or the clinician operation device 320. As another example, the data processing system 344 can process the data gathered by the activity monitoring device 120 and the offloading monitoring device 132 to identify events of interest, such as events that may indicate excessive pressure being placed on the body part 110, and may share the events of interest with the user operation device 310 or the clinician operation device 320.

The network 330 can be a computer network, such as or may include a cellular communications network. Although the network 330 is shown as one connected network, the network 330 can be subdivided into one or more separate networks which may not directly communicate with one another. For example, the device management system 340 can communicate with the user operation device 310 via a separate and different network from the network that the device management system 340 uses to communication with the clinician operation device 320.

Although certain data processing in the computing environment 300 may be described as being performed by the activity monitoring device 120, the offloading monitoring device 132, the user operation device 310, the clinician operation device 320, or the data processing system 344, the certain data processing can be shifted to a different device or system in the computing environment 300. For example, the user operation device 310 may be described as not processing the data provided by the activity monitoring device 120 and the offloading monitoring device 132 and can instead rely on the data processing system 344 to analyze the data; however, the user operation device 310 can additionally or alternatively analyze the data using similar or different approaches or algorithms to the data processing system 344.

Figure 4:
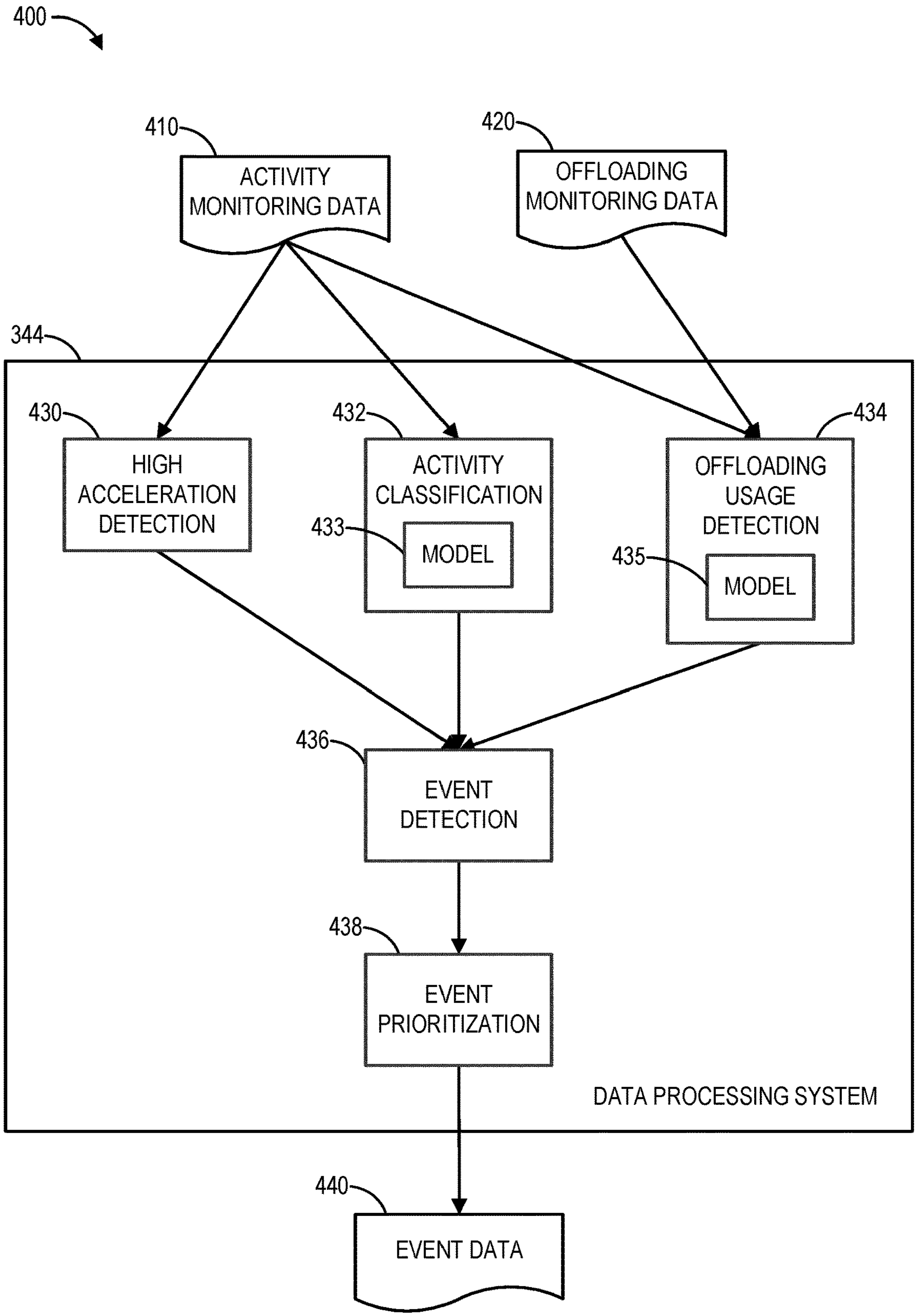
FIG. 4 illustrates example data processing performable within the computing environment of FIG. 3.

FIG. 4 illustrates example data processing 400 by the data processing system 344. As illustrated, activity monitoring data 410 and offloading monitoring data 420 can be received by the data processing system 344. The activity monitoring data 410 and the offloading monitoring data 420 can, in turn, be processed by a high acceleration detection 430, an activity classification 432, and an offloading usage detection 434 of the data processing system 344. The high acceleration detection 430, the activity classification 432, and the offloading usage detection 434 can process individual sets of the activity monitoring data 410 and the offloading monitoring data 420 in parallel or series.

The individual sets can, for example, include the values of the data features determined by the activity monitoring data 410 or the offloading monitoring data 420 for individual data windows. The data windows may correspond to serially-occurring windows of time, such as windows of 10, 25, 50, or 100 milliseconds, 1, 2, 5, 10, 20, or 30 seconds. For example, if a data window of 30 seconds is used, there may be 2 distinct windows for a single minute of data: a first data window encompassing seconds 1-30 and a second data window encompassing seconds 31-60. The next data window may then encompass seconds 1-30 of the next minute of data. The data windows may correspond to sliding windows of time advancing at regular intervals that are less than the total length of an individual data window. For example, if a sliding data window of 30 seconds is used, with the window advancing at 1 second intervals, there may be 31 distinct data windows occurring entirely within a single minute of data: a first data window encompassing seconds 1-30, a second data window encompassing seconds 2-31, a third data window encompassing seconds 3-32, and continuing through to a thirty-first data window encompassing seconds 31-60. A next data window may then encompass seconds 32-60 of the single minute of data, as well as second 1 of a next single minute of data.

Outputs of the high acceleration detection 430, the activity classification 432, and the offloading usage detection 434 can be provided to an event detection 436 of the data processing system 344. The event detection 436 can monitor for individual events on a periodic basis, such as to potentially detect an event up to every 1, 2, 5, 10, 20, 30, 45, or 60 minutes. An output of the event detection 436 can be provided to an event prioritization 438 of the data processing system 344. An output of the event prioritization 438 may be event data 440, which may be further processed by the data processing system 344, stored in the data storage 346, or transmitted (such as via an application program interface (API) of the data processing system 344) to the user operation device 310 or the clinician operation device 320 for processing or display.

The high acceleration detection 430, the activity classification 432, the offloading usage detection 434, the event detection 436, and the event prioritization 438 can each be an algorithm implemented by one or more processors of the data processing system 344 in some aspects.

The activity monitoring data 410 and the offloading monitoring data 420 can be obtained by the communication management system 342 via the network 330, such as from the user operation device 310. The activity monitoring data 410 can include data gathered or determined by the activity monitoring device 120 (such as determined feature data, sensor data, alarms, monitored loading or positioning, or changes to a monitoring or therapy program), as well as and the data collected or determined by the user application 312 (such as user observations, goal information, identifications of activities engaged in by a user, or other information provided by the user related to the activity monitoring device 120). The offloading monitoring data 420 can include data gathered or determined by the offloading monitoring device 132 (such as determined feature data, sensor data, alarms, monitored loading or positioning, or changes to a monitoring or therapy program), as well as and the data collected or determined by the user application 312 (such as user observations, goal information, identifications of activities engaged in by a user, or other information provided by the user related to the activity monitoring device 120 or the offloading monitoring device 132). The high acceleration detection 430, the activity classification 432, and the offloading usage detection 434 can be initiated upon successful receipt or storage of the activity monitoring data 410, the offloading monitoring data 420, or a set thereof by the device management system 340.

The high acceleration detection 430 can process the activity monitoring data 410 to determine whether the activity monitoring device 120 experienced a high acceleration, such as a high instantaneous acceleration or a high average acceleration, for an individual data window. The high acceleration detection 430 can be performed by comparing one or more acceleration values of the activity monitoring data 410 for the individual data window to an acceleration threshold (or thresholds) to determine whether the one or more acceleration values satisfy the acceleration threshold (or thresholds). The acceleration threshold (or thresholds) can, for example, be defined as a multiple of the standard acceleration due to gravity (sometimes referred to as $g_0$ and which has a value of approximately 9.807 $m/s^2$), such as 1.5, 2, 2.5, 3, 3.5, 4, 4.5, or 5 times the standard acceleration due to gravity. The output of the high acceleration detection 430 can be an indication of whether the activity monitoring device 120 experienced the high acceleration during data capture over the individual data window. The output of the high acceleration detection 430 can, for instance, include one or more of sensor ID, user ID, tBodyAcc_mag, sensor timestamp, or assessment time. The output may be organized into a table, list, or an array for the individual data window.

The activity classification 432 can process the activity monitoring data 410 to determine an activity engaged in while wearing or supporting the activity monitoring device 120. The activity classification 432 can, for example, classify the activity for an individual data window or multiple data windows (such as for data corresponding to sensor detection over a period of 30 or 45 seconds or 1, 2, 3, 5, or 10 minutes of data) as one of [i] motion (such as walking or running), [ii] no motion with static weight (such as standing), [iii] no motion with variations in force (such as driving an automobile), or [iv] laying down (such as laying on a flat surface). In general, due to no or little loading of weight on a body part, laying down can be considered to pose no risk to an existing injury (such as an ulcer on the body part) or causing a new injury while motion, no motion with static weight, or no motion with variations in force can be considered to pose a risk to an existing injury or causing a new injury.

The activity classification 432 can be performed using a machine learning technique (such as gradient boosting), a decision tree-based approach, a neural network, or a support vector machine. The activity classification 432 can operate based on an activity classification model 433 (which may also referred to an activity model or, in some instances, a trained activity classification module) used by the activity classification 432 to recognize or distinguish [i] motion, [ii] no motion with static weight, [iii] no motion with variations in force, and [iv] laying down from the activity monitoring data 410, such as from the determined feature data for one or more or all of the data features in Table 1. The activity classification model 433 can, in one example, be a decision tree used by the activity classification 432 to identify the individual data window or multiple data windows of the activity monitoring data 410 as likely corresponding to one of two or more different activities. As another example, the activity classification model 433 can be used by the activity classification 432 to determine a degree to which the individual data window or multiple data windows of the activity monitoring data 410 corresponds to each of two or more different activities, and the activity classification 432 may select the most likely of the different activities to be the classified activity for the individual data window or the multiple data windows.

The activity classification 432 can analyze the activity monitoring data 410 using the activity classification model 433, which can include a decision tree, to determine an activity classification. The decision tree may, for instance, provide that if the activity monitoring data 410 indicates a leg of the user may be elevated, the user may be laying down rather than in motion, no motion with static weight, or no motion with variations in force. The activity classification 432 can determine whether the leg may be elevated from a detected gravity vector and a vector for gravity reference (such as, tGravity_vector) of the activity monitoring data 410, such as by determining an angle between the detected gravity vector and the vector for gravity reference using Equation 1 derived from the dot product of vectors x and y. In one example, the activity classification 432 can determine that the leg may be elevated when the angle between the detected gravity vector and the vector for gravity reference may be at least 30°, 45°, or 60°. The decision tree may, additionally or alternatively, provide that if the activity monitoring data 410 indicates more than a threshold amount of sway over time, the user may not be in no motion with static weight.

$$\theta = \arccos(x \cdot y / |x||y|) \qquad \text{Equation 1}$$

The activity classification 432 can generate activity model input data from the activity monitoring data 410. For example, the activity model input data may include feature data, such as a feature vector that includes data elements representing the data features in Table 1—or some subset thereof—for a particular data window. The activity classification 432 may analyze the activity model input data using the activity classification model 433 to determine an activity classification. The activity classification model 433 may generate activity model output data that represents the likely activity classification(s) of the activity monitoring data 410 from which the activity model input data was generated. For instance, the activity model output data may be a vector, array, or other set of data elements. Individual data elements of the set may correspond to individual activity classifications that the activity classification model 433 is trained to detect. The value of an individual element of the activity model output data may represent the likelihood that the activity model input data represents activity within the activity classification to which the individual data element corresponds. The activity classification that corresponds to the activity model output data element that satisfies one or more classification criteria may be selected as the activity classification for the current data window. Examples of applying classification criteria may include selecting the activity model output data element with the highest value relative to other data elements of the activity model output data or selecting the activity model output data element with a value that satisfies a threshold. The example processing of the activity monitoring data 410 using the activity classification model 433 described herein is illustrative, and is not intended to be limiting or exhaustive. Alternative or additional operations may be used depending upon any of a variety of factors, including a structure of the activity classification model 433, a structure of the activity monitoring data 410, or available computing resources.

The activity classification 432 may store data regarding activity classifications determined for data windows (for example, for individual time periods or time instances). The activity classification 432 can use two or more activity classifications—determined for two or more data windows—to detect a change in the activity classification and output new data responsive to a change in the activity classification. The output of the activity classification 432 can, for instance, include one or more of the following: activity record ID, user ID, activity start time, activity end time, activity duration, activity intensity, or assessment time. A maximum activity change frequency (for instance, such that an activity classification may change no more frequently than every 30 seconds or 1, 2, 5, or 10 minutes) can be set by a user or depend on a previous or newly-determined activity to limit a sensitivity of the activity classification 432 to changes. The activity classification 432 can have a HyperText Transfer Protocol (HTTP) wrapper and be accessible via a HTTP request to a URL.

The offloading usage detection 434 can process the activity monitoring data 410 and the offloading monitoring data 420 to determine whether an offloading device was worn while wearing or supporting the activity monitoring device 120. The offloading usage detection 434 can, for instance, determine whether the offloading device was worn from a comparison of the activity monitoring data 410 and the offloading monitoring data 420, such as a correlation of the activity monitoring data 410 and the offloading monitoring data 420 over an individual data window or multiple data windows (such as for data corresponding to sensor detection over a period of 30 or 45 seconds or 1, 2, 3, 5, or 10 minutes of data). Additionally or alternatively, the offloading usage detection 434 can be performed using a machine learning technique (such as gradient boosting), a decision tree-based approach, a neural network, or a support vector machine. The detection may be made over an individual data window or multiple data windows.

The offloading usage detection 434 can operate based on an offloading usage model 435 used by the offloading usage detection 434 to recognize or distinguish use or non-use of the offloading device from the activity monitoring data 410 and the offloading monitoring data 420, such as from the determined feature data for one or more or all of the data features in Table 1 generated by the activity monitoring device 120 and the offloading monitoring device 132. The offloading usage model 435 can, in one example, be a decision tree used by the offloading usage detection 434 to determine whether the individual data window or multiple data windows of the activity monitoring data 410 or the offloading monitoring data 420 correspond to use or non-use of the offloading device. As another example, the offloading usage model 435 can be used by the offloading usage detection 434 to determine a degree to which the individual data window or multiple data windows of the activity monitoring data 410 and the offloading monitoring data 420 correspond to use or non-use of the offloading device, and the offloading usage detection 434 may select the more likely of use or non-use of the offloading device to be the usage determination for the individual data window or the multiple data windows.

The offloading usage model 435 can be programmed or trained to determine whether the offloading device was likely used during a particular data window. For example, the offloading usage detection 434 may generate a feature vector that includes data elements representing the data features in Table 1—or some subset thereof—for a particular data window of the offloading monitoring data 420. The feature vector may include data elements representing data features of the activity monitoring data 410 for the same or a corresponding data window, one or more data elements representing the output of the activity classification model 433 for the same data window, or one or more data elements representing the activity classification determined by the activity classification 432 for the same data window. The offloading usage model 435 may generate offloading usage model output data. The offloading usage model output data may represent the likelihood that the offloading device was worn during the data window, the degree to which the activity monitoring data 410 and the offloading monitoring data 420 are correlated, or the like. The offloading usage detection 434 may use the offloading usage model output data to determine an offloading usage classification indicating whether the offloading device was likely worn at the time corresponding to the data window.

Additionally or alternatively, the offloading usage detection 434 can analyze the offloading usage model input data using the offloading usage model 435 to determine an activity classification for the offloading monitoring data 420. The activity classification may be compared to the activity classification determined for the activity monitoring data 410 for the same data window. If the activity classifications match or otherwise satisfy one or more correlation criteria, then the offloading usage detection 434 may determine that the offloading device was likely being worn at the time corresponding to the data window. Otherwise, if the activity classifications do not match or otherwise fail to satisfy one or more correlation criteria, then the offloading usage detection 434 may determine that the offloading device likely was not worn at the time corresponding to the data window. The final determination of whether the offloading device was likely worn at the time corresponding to the data window may be an offloading usage classification.

Alternative or additional operations for the offloading usage detection 434 may be used depending upon any of a variety of factors, including a structure of the offloading usage model 435, a structure of the activity monitoring data 410 or the offloading monitoring data 420, or available computing resources.

The offloading usage detection 434 may store data regarding offloading usage determinations for data windows (for example, for individual time periods or time instances). The offloading usage detection 434 may use two or more offloading usage determinations—for two or more data windows—to detect a likely change in offloading usage detection and output new data responsive to a change in the offloading usage detection. The output of the offloading usage detection 434 can, for instance, include one or more of the following: offloading record ID, user ID, assessment time, detection start time, detection end time, or detection duration. A maximum offloading usage change frequency (for instance, such that an offloading usage detection may change no more frequently than every 30 seconds or 1, 2, 5, or 10 minutes) can be set by a user to limit a sensitivity of the offloading usage detection 434 to changes. A correlation window size can be set by a user to control a number of samples from each of the activity monitoring data 410 and the offloading monitoring data 420 that may be processed by the offloading usage detection 434 to determine use or non-use of the offloading device.

The event detection 436 can process the outputs from the high acceleration detection 430, the activity classification 432, and the offloading usage detection 434 to identify one or more events. The one or more events can, for example, each be an instance of (i) a high acceleration determined by the high acceleration detection 430 or (ii) a low acceleration determined by the high acceleration detection 430 along with an activity classification determined by the activity classification 432 and an offloading device non-use determined by the offloading usage detection 434. In some cases, the event detection 436 may not identify an event in response to a determination by the activity classification 432 of laying down or a determination by the offloading usage detection 434 of an offloading device being used. The output of the event detection 436 can, for instance, include one or more of the following: event record ID, event start time, event end time, event peak time, event duration, event impact flag, event classification, or event offloading usage percentage. A maximum event change frequency (for instance, such that a detected event may change no more frequently than every 30 seconds or 1, 2, 5, 10, 20, 30, 45, or 60 minutes) can be set by a user to limit a sensitivity of the event detection 436 to changes or to limit a number of event changes detected per day. The event detection 436 may store and output new data responsive to a change in the activity classified by the activity classification 432, a change in the offloading device usage determined by the offloading usage detection 434, or a detection of the high acceleration by the high acceleration detection 430.

The event prioritization 438 can organize the one or more events identified by the event detection 436 to assist with review of the one or more events. The event prioritization 438 can, for example, prioritize any events that are instances of the high acceleration, as well as a selected number (such as 5, 10, or 15) of any events that are instances of the low acceleration but with a highest associated acceleration magnitude relative to the other events with the low acceleration. The event prioritization 438 can sort or filter the one or more events to help ensure that the one or more events likely to be of greatest interest to the user or a clinician may be brought to the attention of the user or the clinician.

Figure 5:
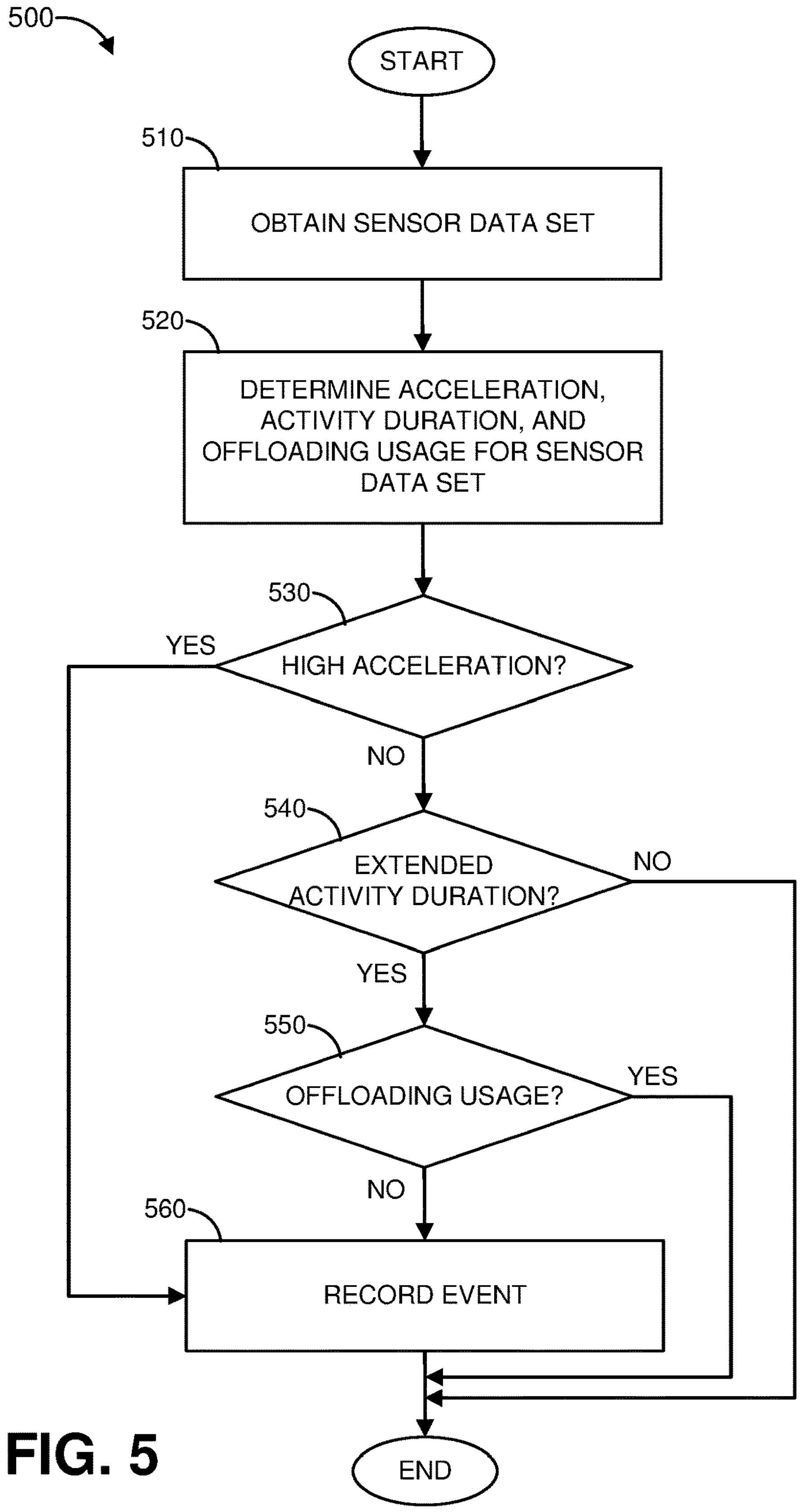
FIG. 5 illustrates an event recordation process performable within the computing environment of FIG. 3.

FIG. 5 illustrates an event recordation process 500 for identifying an event and recording event data associated with the event. For convenience, the event recordation process 500 is described as being performed by the data processing system 344 and in the context of the computing environment 300, but may instead be implemented in other components or systems described herein, or by other computing systems not shown. The event recordation process 500 can advantageously, in certain aspects, facilitate detection of an event during which an individual experienced a loading force which risked adversely impacting an existing injury (such as an ulcer on a foot) or risked causing a new injury (such as a new ulcer on the foot), as well as recordation of associated event information. The event information can, in turn, be used to understand what in a user's lifestyle may impact the existing injury or the new injury and to help with facilitating changes to the user's lifestyle.

At block 510, the event recordation process 500 can obtain a sensor data set. The sensor data set can include, for example, the activity monitoring data 410 and the offloading monitoring data 420, which may include the feature data determined by the activity monitoring device 120 or the offloading monitoring device 132. The sensor data set can be received by the data processing system 344 via the network 330, such as from the user operation device 310, or from the data storage 346. The sensor data set can correspond to and be indicative of motion by or orientation of the activity monitoring device 120 or the offloading monitoring device 132 over a time duration (such as 1, 2, 5, 10, 20, 30, 45, or 60 seconds).

At block 520, the event recordation process 500 can determine an acceleration, an activity duration, and an offloading usage for the sensor data set. The acceleration, the activity duration, and the offloading usage can be determined, for instance, using the high acceleration detection 430, the activity classification 432, and the offloading usage detection 434 of the data processing system 344 as described herein.

At block 530, the event recordation process 500 can determine whether the acceleration determined at block 520 is a high acceleration. For example, the event detection 436 can determine whether the output from the high acceleration detection 430 indicates that the acceleration is the high acceleration.

If the acceleration is the high acceleration, the event recordation process 500 can transition to block 560 and record an event corresponding to the acceleration. For example, the event detection 436 can record the event as event data associated with the event so that the event data may be shared with and reviewed by a user or a clinician in the future to enable the user or the clinician to understand or discuss the event. The event data can be added to a first list. The event data can be the output (or at least part thereof) from the event detection 436.

If the acceleration is not the high acceleration, the event recordation process 500 can transition to block 540 and determine whether the activity duration determined at block 520 is an extended duration. For instance, the event detection 436 can determine whether an activity duration identified by the activity classification 432 satisfies (for instance, lasted) a threshold duration. The threshold duration can depend on an activity (such as motion, no motion with static weight, or no motion with variations in force) determined by the activity classification 432 to be engaged in during the activity duration. Because different activities may have different chances of negatively impacting an existing injury or causing a new injury over time, the threshold duration can be selected for individual activities to correspond to the risks of negative impacts from the individual activities over time. The threshold duration can additionally or alternatively be set according to a user input. If the activity duration is not the extended duration, the event recordation process 500 can end and no event may be recorded for the sensor data set.

If the activity duration is the extended duration, the event recordation process 500 can transition to block 550 and determine whether the offloading usage determined at block 520 indicates usage of an offloading device. For example, the event detection 436 can determine whether the output of the offloading usage detection 434 indicates use of the offloading device. If the offloading usage indicates use of the offloading device (or at least use for a threshold duration or percentage of the activity duration), the event recordation process 500 can end and no event may be recorded for the sensor data set (or window).

If the offloading usage indicates non-use of the offloading device (or at least non-use for a threshold duration or percentage of the activity duration), the event recordation process 500 can transition to block 560 and record an event corresponding to the non-high acceleration, the extended activity duration, and the offloading device non-usage. Event data for this event can be recorded to a second list, which can be the same as or different from the first list. For example, the event detection 436 can record the event as event data associated with the event so that the event data may be shared with and reviewed by a user or a clinician in the future to enable the user or the clinician to understand or discuss the event. The event data can be the output (or at least part thereof) from the event detection 436.

The event recordation process 500 can be repeated for one or more additional sensor data sets so that the event recordation process 500 may be used to record events for the activity monitoring device 120 or the offloading monitoring device 132.

The data processing 400 or the event recordation process 500 can advantageously, in certain aspects, process an extensive volume of the activity monitoring data 410 and the offloading monitoring data 420 to detect and prioritize among hundreds, thousands, or more events for recording or presentation to the clinician or user. The events may indicate a risk of adversely impacting an existing injury or developing a new injury, such as to a user's skin. The events can include [i] high acceleration events or [ii] events corresponding to the non-high acceleration, extended activity duration (such as with the activity being an activity other than laying down), and offloading device non-usage during the duration of the activity. The events prioritized by the data processing 400 or the event recordation process 500 can desirably support discussion or actions which result in behavior changes that limit the risk of adversely impacting the existing injury or developing the new injury.

Computer System Components

Figure 6:
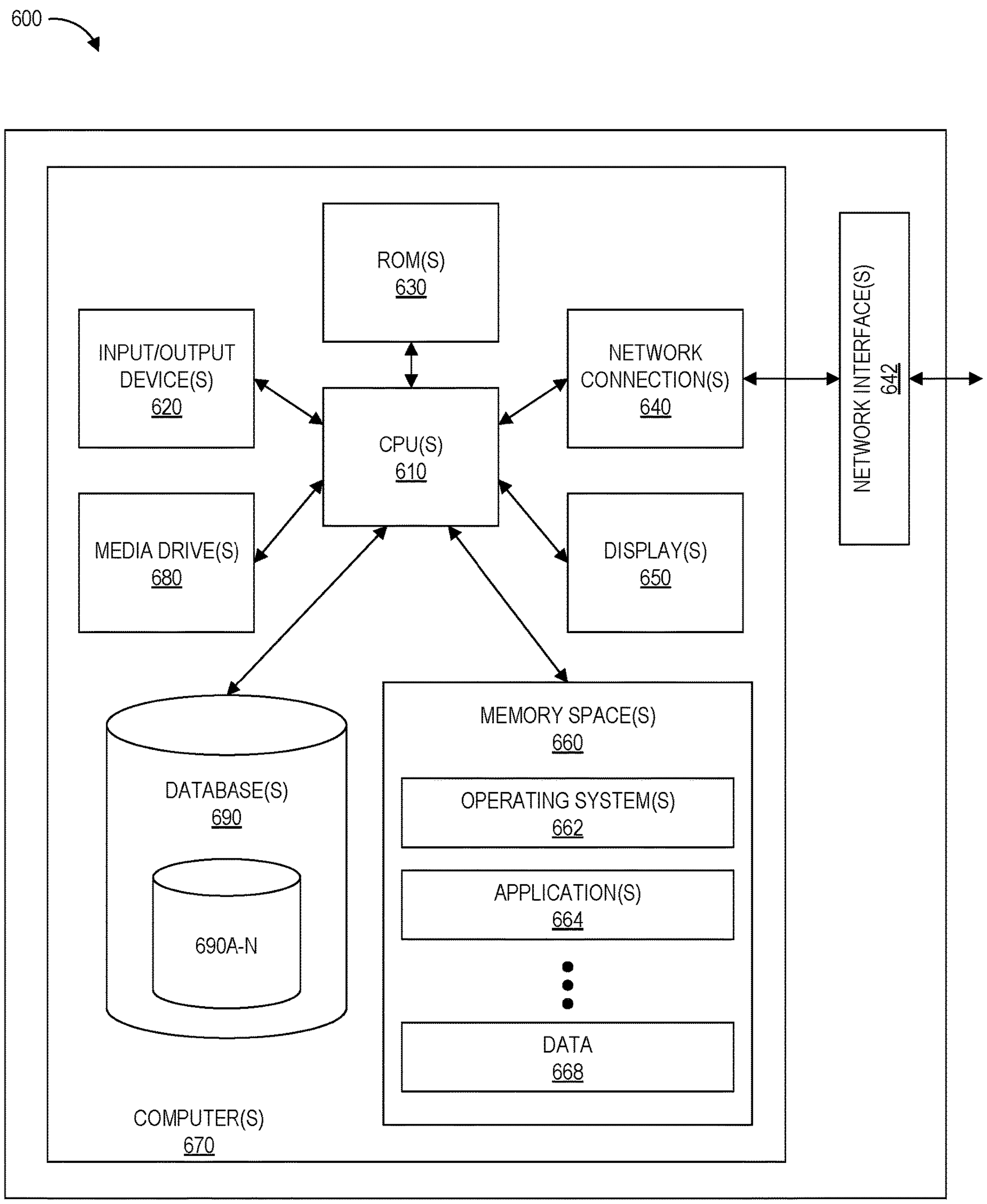
FIG. 6 illustrates an example computer system usable to construct one or more of the devices or systems within the computing environment of FIG. 3.

FIG. 6 illustrates a computer system 600 usable to construct one or more of the devices (for instance, the user operation device 310 or the clinician operation device 320), systems (for instance, the device management system 340), servers, or the like within the computing environment 300 of FIG. 3.

As shown in FIG. 6, the computer system 600 can include (i) a processor(s) (CPUs) 610, (ii) an input/output device(s) 620 configured to allow users to input and output information and interact with the computer system 600 as well as transfer and receive data or capture data with one or more sensors like an image sensor, (iii) a read only memory device(s) (ROMs) 630 or equivalents to provide nonvolatile storage of data or programs, (iv) a display(s) 650 such as a computer monitor or other display device, (v) a network connection(s) 640 and a network interface(s) 642 configured to allow the computer system 600 to connect to other systems, servers, or portable devices, as well as a memory space(s) 660 and a database(s) 690. The database(s) 690 may be further divided or distributed as sub-database(s) 690A-690N, with the sub-database(s) storing feature or function specific information associated with a particular feature or function. The various components shown in FIG. 6 may be incorporated in a computer(s) 670. It is noted that the various components shown in FIG. 6, including the database(s) 690, are typically included as part of the computer(s) 660, however, they may be external to the computer(s) 670 in some aspects. For example, the database(s) 690 may be external to the computer(s) 670 and may be part of a separate database computer system or networked database system. In some instances, the computer system 600 may be a computing device like a desktop computer, mobile phone, or a server.

The memory space(s) 660 may include DRAM, SRAM, FLASH, hard disk drives, or other memory storage devices, such as a media drive(s) 680, configured to store an operating system(s) 662, an application program(s) 664, and data 668, and the memory space(s) 660 may be shared with, distributed with or overlap with the memory storage capacity of the database(s) 690. In some aspects, the memory space(s) 660 may include the database(s) 690 or in some aspects the database(s) 690 may include the data 668 as shown in the memory space(s) 660. The data stored in the memory space(s) 660 or the database(s) 690 may include information, such as sensor data, pairing program information, data processing routines, or other types of data described herein.

Other Variations and Terminology

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines or computing systems that can function together.

One or more user inputs described in this disclosure may be received using one or more different mechanisms. For example, user interface controls may be selected by a user using one or more input options, such as a mouse, touch screen input, or keyboard input, among other user interface input options. The user interface controls selected by the user can include one or more of buttons, dropdown boxes, select boxes, text boxes, check boxes, slider controls, or other user interface controls.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, a microprocessor, a state machine, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A hardware processor can include electrical circuitry or digital logic circuitry configured to process computer-executable instructions. In another aspect, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "e.g.," and the like, unless specifically stated otherwise, or otherwise understood within the context as used, is generally intended to convey that certain aspects include, while other aspects do not include, certain features, elements or states. Thus, such conditional language is not generally intended to imply that features, elements or states are in any way required for one or more aspects or that one or more aspects necessarily include logic for deciding, with or without author input or prompting, whether these features, elements or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments described herein can be embodied within a form that does not provide all of the features and benefits set forth herein, as some features can be used or practiced separately from others.

What is claimed is:

1. A system for gathering and processing sensor data to identify a risk of impacting or causing a skin injury, the system comprising computer-readable memory and one or more processors, the system being configured to:

obtain sensor feature data comprising a first set of feature data and a second set of feature data, the first set of feature data representing output of a user sensor worn on a limb of a user, the user sensor not coupled to an offloading device worn on the limb, the second set of feature data representing output of an offloading device sensor coupled to the offloading device;

determine an activity classification using the first set of feature data input into an activity classification model, wherein the activity classification model is configured to determine a first degree of similarities between the first set of feature data and each of a plurality of different activity classifications, and wherein the activity classification is determined based on the first degree of similarities;

determine an offloading usage classification using the first set of feature data and the second set of feature data input into an offloading usage model, wherein the offloading usage model is configured to determine a second degree of similarities between motion of the user sensor associated with the first set of feature data and motion of the offloading device sensor associated with the second set of feature data, and wherein the offloading usage classification is determined based on the second degree of similarities;

from a plurality of events represented in the sensor feature data, identify a set of events for which at least one of 1) the activity classification satisfies an acceleration threshold or 2) the activity classification satisfies a duration threshold and the offloading usage classification indicates that the offloading device was not used during an event;

generate display data comprising the set of events, the set of events associated with the risk of impacting or causing the skin injury on the limb; and transmit the display data to a computing device and cause the computing device to present the display data.

2. The system of claim 1, wherein the skin injury comprises a diabetic foot ulcer or a venous leg ulcer.

3. The system of claim 1, wherein the user sensor comprises a first accelerometer and a first magnetometer, and the offloading device sensor comprises a second accelerometer and a second magnetometer, the first set of sensor feature data representing output from the first accelerometer and the first magnetometer, and the second set of sensor feature data representing output from the second accelerometer and the second magnetometer.

4. The system of claim 1, being further configured to:

determine a subsequent activity classification using a third set of feature data input into the activity classification model, the third set of feature data representing output of the user sensor; and determine from the activity classification and the subsequent activity classification that a change in an activity of the user has occurred.

5. The system of claim 1, being further configured to:

determine a subsequent offloading usage classification using a third set of feature data and a fourth set of feature data input into the offloading usage model, wherein the third set of feature data represents output of the user sensor, and the fourth set of feature data represents output of the offloading device sensor; and determine from the offloading usage classification and the subsequent offloading usage classification that a change usage of the offloading device by the user has occurred.

6. The system of claim 1, being further configured to:

generate activity model input data using the first set of feature data;

generate activity classification model output data using the activity model input data input into the activity classification model; and identify, from the activity classification model output data, a data element having a value that satisfies a classification criterion to determine the activity classification, the activity classification being associated with the data element.

7. The system of claim 1, wherein the plurality of different activity classifications comprises a motion classification, a no motion with static weight classification, a no motion with variations in force classification, and a laying down classification.

8. The system of claim 1, wherein the offloading usage model is configured to determine the second degree of similarities from the degree to which motion and orientation of the user sensor corresponds to motion and orientation of the offloading device sensor.

9. The system of claim 1, wherein the activity classification model comprises a decision tree, a neural network, or a support vector machine.

10. The system of claim 1, wherein the activity classification model comprises a first decision tree configured to assign the first set of feature data to one of the plurality of different activity classifications for the first degree of similarities, and the offloading usage model comprises a second decision tree configured to determine whether motion and orientation of the user sensor corresponds to motion and orientation of the offloading device sensor for the second degree of similarities.

11. The system of claim 1, wherein the limb comprises a leg of the user, and the user sensor is worn below a knee of the leg of the user.

12. A computer-implemented method for gathering and processing sensor data to identify a risk of impacting or causing a skin injury, the computer-implemented method comprising:

receiving, via a computer network, sensor feature data representing output of a user sensor worn on a limb of a user, the user sensor not coupled to an offloading device worn on the limb;

generating, by one or more computer processors, activity classification model output data using the sensor feature data input into an activity classification model, the activity classification model output data representing likelihoods determined by the activity classification model that the sensor feature data corresponds to each of a plurality of different activity classifications, wherein the plurality of different activity classifications comprises:

a first activity classification representing motion of the limb; and a second activity classification representing no motion of the limb with weight loading the limb;

determining, by the one or more computer processors, an activity classification from the activity classification model output data associated with the risk of impacting or causing the skin injury on the limb; and transmitting, via the computer network, display data comprising the activity classification to a computing device and causing the computing device to present the display data.

13. A non-transitory computer readable medium having an application stored thereon for gathering and processing sensor data to identify a risk of impacting or causing a skin injury, the application, when executed by one or more computer processors, causing the one or more computer processors to:

receive, via a computer network, sensor feature data representing output of a user sensor worn on a limb of a user, the user sensor not coupled to an offloading device worn on the limb;

generate activity classification model output data using the sensor feature data input into an activity classification model, the activity classification model output data representing likelihoods determined by the activity classification model that the sensor feature data corresponds to each of a plurality of different activity classifications, wherein the plurality of different activity classifications comprises:

a first activity classification representing motion of the limb; and a second activity classification representing no motion of the limb with weight loading the limb;

determine an activity classification from the activity classification model output data associated with the risk of impacting or causing the skin injury on the limb; and transmit, via the computer network, display data comprising the activity classification to a computing device and cause the computing device to present the display data.

14. The non-transitory computer readable medium of claim 13, wherein the plurality of different activity classifications comprises a third activity classification representing no motion of the limb with variations in force on the limb.

15. The non-transitory computer readable medium of claim 13, wherein the plurality of different activity classifications comprises a third activity classification representing the user is lying down.

16. The non-transitory computer readable medium of claim 13, wherein the activity classification model comprises a decision tree, a neural network, or a support vector machine.

17. The non-transitory computer readable medium of claim 13, wherein the activity classification model comprises a decision tree configured to assign the sensor feature data to one of the plurality of different activity classifications.

18. The non-transitory computer readable medium of claim 13, wherein the application, when executed by the one or more computer processors, further causes the one or more computer processors to:

determine a subsequent activity classification using second sensor feature data input into the activity classification model, the second sensor feature data representing output of the user sensor; and determine from the activity classification and the subsequent activity classification that a change in an activity of the user has occurred.

19. The non-transitory computer readable medium of claim 13, wherein the application, when executed by the one or more computer processors, further causes the one or more computer processors to:

receive, via the computer network, second sensor feature data representing output of an offloading device sensor coupled to the offloading device; and determine an offloading usage classification using the sensor feature data and the second sensor feature data input into an offloading usage model, wherein the offloading usage model is configured to determine a degree to which motion of the user sensor corresponds to motion of the offloading device sensor.

20. The non-transitory computer readable medium of claim 19, wherein the offloading usage model is configured to determine the degree to which motion and orientation of the user sensor corresponds to motion and orientation of the offloading device sensor.

21. The non-transitory computer readable medium of claim 19, wherein the application, when executed by the one or more computer processors, further causes the one or more computer processors to:

receive, via the computer network, third sensor feature data representing output of the offloading device sensor coupled to the offloading device;

determine a subsequent offloading usage classification using third sensor feature data input into the offloading usage model, the third sensor feature data representing output of the offloading device sensor; and determine from the offloading usage classification and the subsequent offloading usage classification that a change in usage of the offloading device by the user has occurred.

* * * * *